(12) United States Patent
Nakamura

(10) Patent No.: US 11,273,002 B2
(45) Date of Patent: Mar. 15, 2022

(54) DISPLAY SYSTEM

(71) Applicant: Panasonic Corporation, Osaka (JP)

(72) Inventor: Masaaki Nakamura, Osaka (JP)

(73) Assignee: PANASONIC CORPORATION, Osaka (JP)

( * ) Notice: Subject to any disclaimer, the term of this patent is extended or adjusted under 35 U.S.C. 154(b) by 0 days.

(21) Appl. No.: 16/359,285

(22) Filed: Mar. 20, 2019

(65) Prior Publication Data
US 2019/0216573 A1 Jul. 18, 2019

Related U.S. Application Data

(63) Continuation of application No. PCT/JP2017/024846, filed on Jul. 6, 2017.

(30) Foreign Application Priority Data

Sep. 28, 2016 (JP) .............................. JP2016-190168

(51) Int. Cl.
A61B 90/00 (2016.01)
H04N 9/31 (2006.01)
(Continued)

(52) U.S. Cl.
CPC ............ A61B 90/37 (2016.02); A61B 1/0005 (2013.01); A61B 1/043 (2013.01); H04N 5/272 (2013.01);
(Continued)

(58) Field of Classification Search
None
See application file for complete search history.

(56) References Cited

U.S. PATENT DOCUMENTS 10,639,104 B1 * 5/2020 Barral ................. A61B 90/36
2008/0004533 A1 * 1/2008 Jansen ................. A61B 5/415
600/476
(Continued)

FOREIGN PATENT DOCUMENTS

JP 2005-21453 1/2005
JP 2006-180926 7/2006
(Continued)

OTHER PUBLICATIONS

International Search Report dated Sep. 19, 2017 in International (PCT) Application No. PCT/JP2017/024846.
(Continued)

Primary Examiner — Rebecca A Volentine
(74) Attorney, Agent, or Firm — Wenderoth, Lind & Ponack, L.L.P.

(57) ABSTRACT

A display system includes an irradiator, an imager, an image generator, a projector, a display, and an adjuster. The irradiator irradiates an object with light having a wavelength in an invisible light region. The imager captures an invisible light image based on light excited by the light having the wavelength in the invisible light region, and a visible light image based on light in a visible light region, in the object. The image generator generates a projection image based on the invisible light. The projector projects the projection image onto the object with visible light. The display displays the invisible light image, the visible light image and the projection image in a superimposed manner with each other. The adjuster adjusts the projection image on the display, based on a user operation. The projector projects the projection image adjusted by the adjuster.

4 Claims, 16 Drawing Sheets

(51) Int. Cl.
*H04N 7/18* (2006.01)
*H04N 5/272* (2006.01)
*A61B 1/00* (2006.01)
*A61B 1/04* (2006.01)

(52) U.S. Cl.
CPC .......... *H04N 7/183* (2013.01); *H04N 9/3182* (2013.01); *A61B 2090/366* (2016.02); *A61B 2090/373* (2016.02)

(56) References Cited

U.S. PATENT DOCUMENTS

| | | |
|---|---|---|
| 2009/0202119 A1 | 8/2009 | Hefti et al. |
| 2012/0268573 A1 | 10/2012 | Schönborn et al. |
| 2014/0052002 A1* | 2/2014 | Lee ...................... A61B 5/7271 600/473 |
| 2014/0085448 A1 | 3/2014 | Mitamura |
| 2014/0254953 A1 | 9/2014 | Sato |
| 2015/0051617 A1 | 2/2015 | Takemura et al. |
| 2016/0252716 A1 | 9/2016 | Nakamura et al. |
| 2016/0262626 A1* | 9/2016 | Pelosi .................. A61B 5/0059 |
| 2017/0042631 A1* | 2/2017 | Doo ...................... A61B 90/37 |
| 2017/0079741 A1* | 3/2017 | Makinouchi ........... A61B 90/36 |
| 2018/0270474 A1* | 9/2018 | Liu ..................... G06K 9/00201 |
| 2018/0288404 A1* | 10/2018 | Ikehara ................ H04N 13/341 |

FOREIGN PATENT DOCUMENTS

| | | |
|---|---|---|
| JP | 5798430 | 8/2015 |
| WO | 2013/145730 | 10/2013 |
| WO | 2015/072047 | 5/2015 |

OTHER PUBLICATIONS

Extended European Search Report dated Sep. 24, 2019 in corresponding European Patent Application No. 17855349.1.
International Preliminary Report on Patentability dated Apr. 11, 2019 in International (PCT) Application No. PCT/JP2017/024846.
Communication pursuant to Article 94(3) EPC dated Jun. 23, 2020 in European Application No. 17 855 349.1.
Office Action dated Dec. 7, 2020 in European Application No. 17 855 349.1.
Office Action dated Aug. 24, 2021 in European Application No. 17855349.1.
Communication pursuant to Article 94(3) EPC dated Jan. 3, 2022 in European Patent Application No. 17 855 349.1.

* cited by examiner

DISPLAY SYSTEM

BACKGROUND

1. Technical Field

The present disclosure relates to a display system for displaying a display image.

2. Related Art

JP 5798430 B2 discloses a fluorescent light observation device that is used in a medical field and the like. In JP 5798430 B2, an observation light source and an imaging device are used to alternately capture two types of original images, that is, an image in a state where fluorescence is generated by supplying excitation light and a background image in a state where excitation light is not supplied. The fluorescent light observation device of JP 5798430 B2 extracts an image component of fluorescence by generating a difference image between the two types of original images. In JP 5798430 B2, in order to observe a time change and the like of weak fluorescence in an observation object in real time, an intensity distribution and the like of fluorescence obtained by binarizing the difference image are displayed on the original image from the imaging device.

SUMMARY

An object of the present disclosure is to provide a display system capable of facilitating adjustment of an image in a display system for displaying the image based on a captured image.

A display system according to the present disclosure includes an irradiator, an imager, an image generator, a projector, a display, and an adjuster. The irradiator irradiates an object with light having a wavelength in an invisible light region. The imager captures an invisible light image and a visible light image in the object, the invisible light image based on light excited by the light having the wavelength in the invisible light region, and the visible light image based on light in a visible light region. The image generator generates a projection image based on the invisible light. The projector projects the projection image onto the object with visible light. The display displays the invisible light image, the visible light image and the projection image in a superimposed manner with each other. The adjuster adjusts the projection image on the display, based on a user operation. The projector projects the projection image adjusted by the adjuster.

According to the display system, the adjustment of the image in the display system for displaying the display image based on the capture image can be facilitated.

BRIEF DESCRIPTION OF DRAWINGS

FIG. 43 is a view illustrating a state of a surgical field upon projection in the surgery supporting system.

DESCRIPTION OF EMBODIMENTS

Hereinafter, embodiments will be described in detail with reference to the drawings as appropriate. However, detailed descriptions more than necessary may be omitted. For example, detailed descriptions of well-known matters and redundant descriptions for substantially the same configuration may be omitted. This is to avoid unnecessary redundancy of the following description and to facilitate understanding by those skilled in the art.

It is to be noted that the applicant provides the accompanying drawings and the following description in order to enable those skilled in the art to fully understand the present disclosure, and does not intend to limit the claimed subject matter by them.

First Embodiment

As a specific example of a display system according to the present disclosure, a surgery supporting system will be described.

1. Configuration 1-1. Outline of Surgery Supporting System

Figure 1:
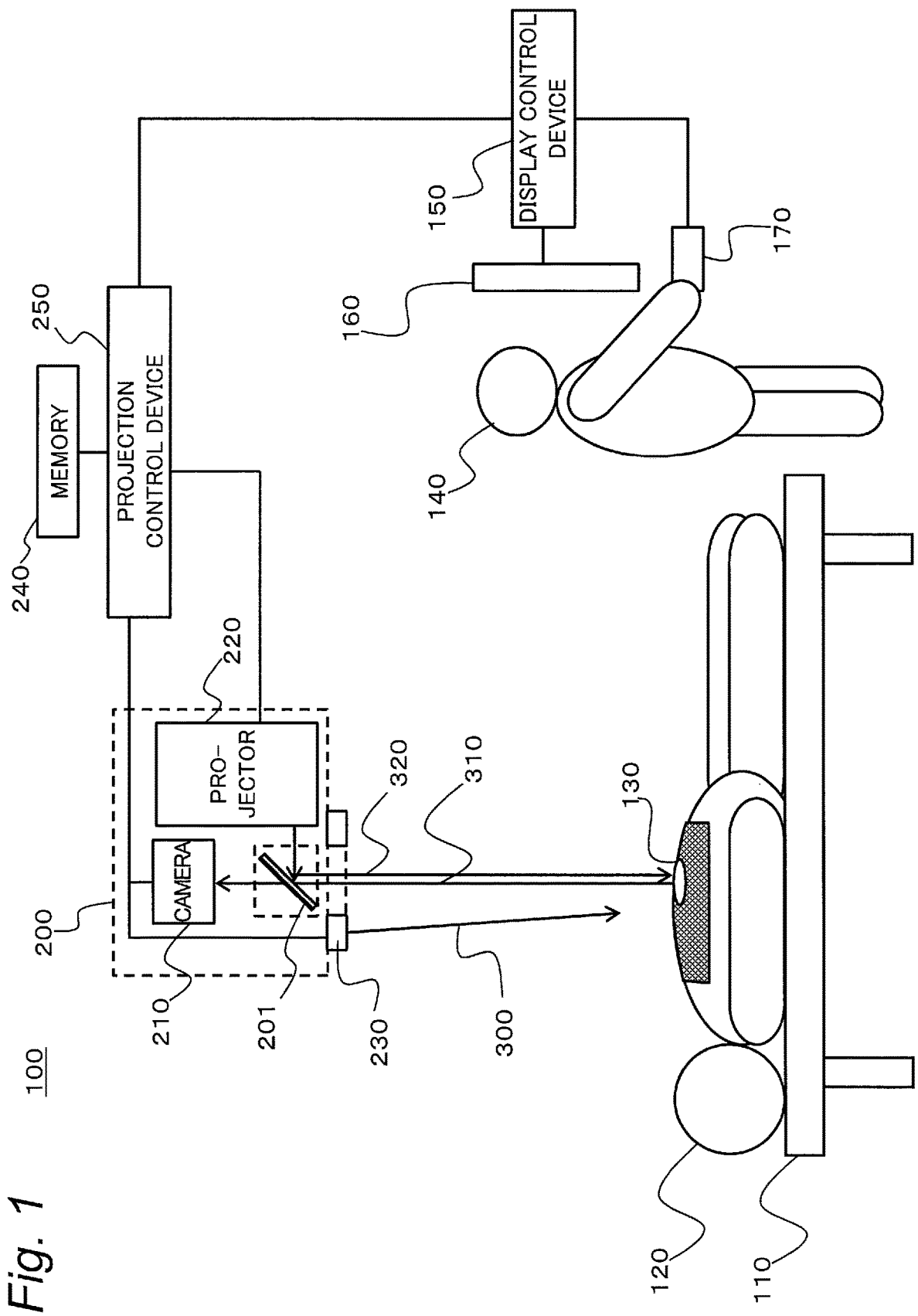
FIG. 1 is a schematic diagram showing a configuration of a surgery supporting system according to a first embodiment.

An outline of a surgery supporting system according to a first embodiment will be described with reference to FIG. 1. FIG. 1 is a schematic diagram showing a configuration of a surgery supporting system 100 according to the first embodiment.

The surgery supporting system 100 includes a camera 210, a projector 220, and an excitation light source 230. The surgery supporting system 100 visually supports surgery performed by a doctor or the like on a patient in an operating room or the like, by using projection images. When using the surgery supporting system 100, a photosensitive substance is administered in advance to a patient 120 who is undergoing surgery.

The photosensitive substance is a substance that emits fluorescence in response to excitation light. As the photosensitive substance, for example, indocyanine green (ICG), aminolevulinic acid (5-ALA), porphyrin, or the like is used. In the present embodiment, a description is given to a case where ICG is used as an example of the photosensitive substance. ICG emits fluorescence in an infrared region at a wavelength of 820 to 860 nm, by irradiation with excitation light in an infrared region around a wavelength of 780 nm.

When administered to the patient 120, the photosensitive substance accumulates in an affected part 130 where a flow of blood or lymph is stagnant. Therefore, detecting a region emitting fluorescence in response to the irradiation of the excitation light enables identification of a region of the affected part 130.

Here, the fluorescence emitted by the affected part 130 may be weak, or a wavelength band of the fluorescence may be in an invisible region or around the invisible region. Therefore, identification of the region of the affected part 130 is difficult even if the doctor visually observes a surgical field 135. To solve this problem, the surgery supporting system 100 uses the camera 210 to identify the region of the affected part 130 emitting fluorescence light 310. Further, projection light 320 of visible light is emitted from the projector 220 to the affected part 130 so as to allow a person to visually recognize the identified affected part 130. Accordingly, projection of a projection image that visualizes the identified region of the affected part 130 is achieved, and this enables support of the identification of the region of the affected part 130 by the doctor or the like who performs surgery.

1-2. Configuration of Surgery Supporting System

Hereinafter, a configuration of the surgery supporting system 100 will be described with reference to FIG. 1. The surgery supporting system 100 is disposed within an operating room of a hospital, to be used. The surgery supporting system 100 includes an imaging irradiation device 200, a memory 240, and a projection control device 250.

Although not shown in the drawings, the surgery supporting system 100 also includes a mechanism to change an arrangement of the imaging irradiation device 200, for example, a drive arm mechanically connected to the imaging irradiation device 200, a caster of a base to be placed with a set of the surgery supporting system 100, and the like. With the above mechanism, the imaging irradiation device 200 is arranged vertically above a surgical bed 110 on which the patient 120 is placed or above the surgical bed 110 with an angle from the vertical direction. In addition, the surgical bed 110 may include a driving mechanism capable of changing a height and a direction.

The imaging irradiation device 200 is a device in which the camera 210, the projector 220, and the excitation light source 230 are integrally assembled together with an optical unit 201. Details of a configuration of the imaging irradiation device 200 will be described later.

The memory 240 is a storage medium to which the projection control device 250 accesses during execution of various operations. The memory 240 is configured with, for example, a ROM and a RAM. The memory 240 is an example of a storage in the present embodiment.

The projection control device 250 integrally controls each of devices constituting the surgery supporting system 100. The projection control device 250 is electrically connected to the camera 210, the projector 220, the excitation light source 230, and the memory 240, and outputs control signals for controlling each device. The projection control device 250 is configured with, for example, a CPU, and realizes a function of the projection control device 250 by executing a predetermined program. The function of the projection control device 250 may be realized by an electronic circuit designed exclusively or a reconfigurable electronic circuit (FPGA, ASIC, or the like).

For example, the projection control device 250 performs various kinds of image processing on a captured image of the camera 210 to generate a video signal (image data) indicating a projection image. The projection control device 250 is an example of an image generator in the present disclosure.

Further, in the present embodiment, the surgery supporting system 100 includes a display control device 150, a monitor 160, and a mouse 170.

The display control device 150 is configured with, for example, a personal computer (PC), and is connected to the projection control device 250. The display control device 150 includes, for example, a CPU, and performs image processing and the like for generating an image to be displayed on the monitor 160. The display control device 150 is an example of an image generator in the present disclosure. Further, the display control device 150 includes an internal memory (ROM, RAM, and the like), which is an example of a storage in the present disclosure.

The monitor 160 is configured with, for example, a liquid crystal display or an organic EL display, and has a display surface for display of an image. The monitor 160 is an example of a display in the present disclosure.

The mouse 170 is used by a user to input operations to the display control device 150. The mouse 170 is an example of an adjuster in the present disclosure. Instead of or in addition to the mouse 170, the surgery supporting system 100 may include various adjusters, e.g. a keyboard, a touch pad, a touch panel, a button, a switch, and the like.

An operator 140 (user) of the display control device 150 can confirm a capture image by the camera 210 on the monitor 160 during surgery, for example. In addition, the operator 140 can adjust various kinds of setting of a projection image (e.g., a threshold value for intensity distribution of fluorescence).

1-3. Configuration of Imaging Irradiation Device

Figure 2:
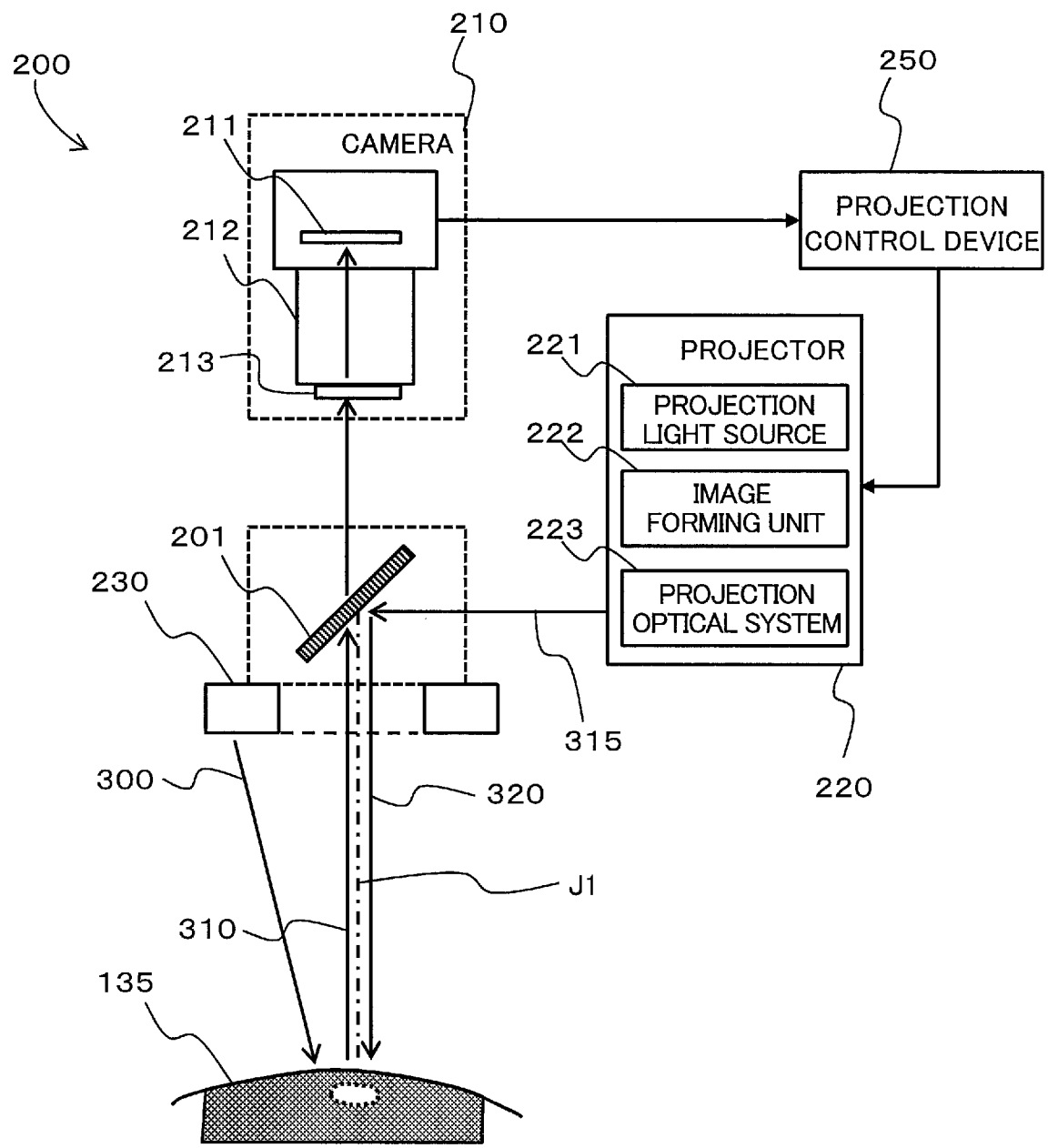
FIG. 2 is a block diagram showing a configuration of an imaging irradiation device in the surgery supporting system.

Next, a configuration of the imaging irradiation device 200 will be described in detail with reference to FIG. 2. FIG. 2 is a block diagram showing a configuration of the imaging irradiation device 200 in the surgery supporting system.

The excitation light source 230 is a light source device that emits excitation light 300 to cause a photosensitive substance to emit fluorescence. In this embodiment, since ICG is used as the photosensitive substance, the excitation light source 230 emits the excitation light 300 of a wavelength band (e.g., around 780 nm) including an excitation wavelength of ICG. The excitation light source 230 is an example of an irradiator in the present embodiment. The excitation light source 230 switches ON/OFF of emission of the excitation light 300 in accordance with the control signal from the projection control device 250. Note that the excitation light source 230 may be configured separately from the imaging irradiation device 200.

The camera 210 captures an image of an object including the surgical field 135 and the like of the patient 120 to generate a capture image. The camera 210 transmits image data indicating the generated capture image to the projection control device 250. This embodiment uses, as the camera 210, a camera capable of capturing an image on the basis of light in the wavelength band of 820 nm to 860 nm of ICG fluorescence, together with a visible light region. The camera 210 is an example of an imager in the present embodiment. As shown in FIG. 2, the camera 210 includes an image pickup element 211, a telephoto lens 212, and an optical filter 213.

The image pickup element 211 is configured with, for example, a CCD image sensor or a CMOS image sensor. The image pickup element 211 has an imaging surface on which light incident from the telephoto lens 212 forms an image.

The telephoto lens 212 includes a zoom lens to set an angle of view of the camera 210, and a focus lens to adjust a focus. The telephoto lens 212 is an example of an imaging optical system in the camera 210. Instead of the telephoto lens 212, a standard lens, a medium telephoto lens, or a super telephoto lens may be used.

As shown in FIG. 2, the optical filter 213 is disposed on an incident surface of the telephoto lens 212. The optical filter 213 includes a band pass filter that transmits, among incident light, a wavelength band component (e.g., around 850 nm) that allows fluorescence to be generated from a photosensitive substance such as ICG, but blocks other wavelength band components. This enables the camera 210 to capture images based on fluorescence of ICG and the like.

The camera 210 may have a function of capturing an image based on visible light, excitation light, or the like, in addition to an image based on fluorescence. In this case, the optical filter 213 may further include a filter that blocks a wavelength band component for fluorescence described above and that transmits a wavelength band component of the visible light or the excitation light, and a filter switching mechanism for respective filters. The filter switching mechanism switches insertion/extraction of the respective filters for incident light to the telephoto lens 212, in accordance with the control signal from the projection control device 250, for example. The camera 210 is an example of an object imager that captures an image representing an object on the basis of visible light, excitation light, or the like.

The projector 220 is a projector of, for example, a DLP system, a 3LCD system, an LCOS system, or the like. The projector 220 emits projection light 315 so as to project, with visible light, a projection image based on a video signal input from the projection control device 250. The projector 220 is an example of a display that displays a projection image on the projection surface in the present embodiment. As shown in FIG. 2, the projector 220 includes a projection light source 221, an image forming unit 222, and a projection optical system 223.

The projection light source 221 is configured with, for example, a semiconductor laser (LD), LED, a halogen lamp, or the like. The projection light source 221 emits visible light to the image forming unit 222. The projection light source 221 may have, as appropriate in accordance with the projection system of the projector 220, a light source element of a single color alone, or may have a light source element of plural colors such as RGB, or a white light source element.

The image forming unit 222 includes a spatial light modulation element such as a DMD or an LCD. The image forming unit 222 forms an image based on a video signal from the projection control device 250, on an image formation surface of the spatial light modulation element. When light from the projection light source 221 is spatially modulated in accordance with the image foiled in the image forming unit 222, the projection light 315 is generated.

The projection optical system 223 includes a zoom lens to set an angle of view of the projector 220 and a focus lens to adjust a focus. Further, the projection optical system 223 may incorporate a lens shifting mechanism to shift various lens positions.

Moreover, the projector 220 may include a projection control circuit that realizes functions peculiar to the projector 220, such as keystone correction and lens shifting function, for example. Further, each of the above functions may be realized in the projection control device 250.

In addition, the projector 220 may be of a laser scanning type, or may be configured to include a galvano mirror or a MEMS mirror that can be driven in a scanning direction.

For example, the optical unit 201 is configured with a dichroic mirror that has optical characteristics of transmitting a specific wavelength band component of incident light and reflecting other wavelength band components. For example, the optical unit 201 transmits light of a wavelength band component exceeding 650 nm (including fluorescence of ICG), and reflects light of a wavelength band component lower than 650 nm (including visible light).

The optical characteristics of the optical unit 201 can be set as appropriate in accordance with the fluorescence characteristics of the photosensitive substance to be used. Further, when the camera 210 has a function of capturing the image by visible light, the optical unit 201 can be configured to transmit a part of visible light. For example, the optical unit 201 may have optical characteristics of transmitting a part of a wavelength band component in the visible light region, or a transmittance of visible light may be set within a range lower than a reflectance.

As shown in FIG. 2, the optical unit 201 is arranged to face each of the camera 210 and the projector 220. Due to the above optical characteristics, the optical unit 201 transmits the fluorescence light 310 directed toward the imaging surface of the camera 210, while reflecting the projection light 315 emitted from the projector 220. The reflected projection light 320 is emitted onto the surgical field 135.

In the present embodiment, the optical unit 201 guides light such that an optical axis of incident light incident on the camera 210, such as the fluorescence light 310 from the surgical field 135, is coincident with an optical axis of the projection light 320 projecting a projection image on the surgical field 135, on an optical axis J1. This can reduce a positional deviation of the projection image based on the capture image by the camera 210.

For the coincidence of the optical axes in the present disclosure, an allowable error may be set as appropriate. For example, the optical axes may coincide with each other within the allowable error such as within an angle range of ±5 degrees or within an interval range of 1 cm between the optical axes.

2. Operation

Hereinafter, an operation of the surgery supporting system 100 according to the present embodiment will be described.

2-1. Normal Mode Operation

An operation of the surgery supporting system 100 in a normal mode will be described with reference to FIGS. 3, 4A, and 4B. The normal mode is an operation mode for performing a basic projecting operation for supporting surgery in the surgery supporting system 100.

Figure 3:
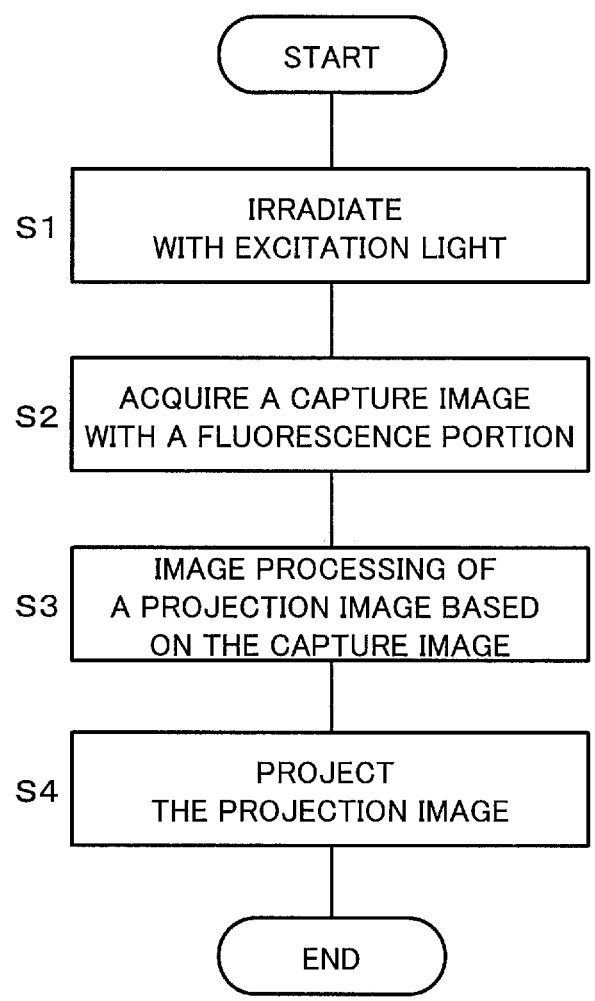
FIG. 3 is a flowchart for explaining an operation in a normal mode in the surgery supporting system.

FIG. 3 is a flowchart for explaining an operation in the normal mode in the surgery supporting system 100. FIG. 4A shows a state of the surgical field 135 in the surgery supporting system 100 before performing the projecting operation in the normal mode. FIG. 4B shows a state where the projecting operation is performed on the surgical field 135 in FIG. 4A.

The flowchart of FIG. 3 is executed by the projection control device 250. The processing according to this flowchart is performed in a state where the optical filter 213 of the camera 210 is set to block visible light and excitation light and to transmit the fluorescence light 310.

Figure 4A:
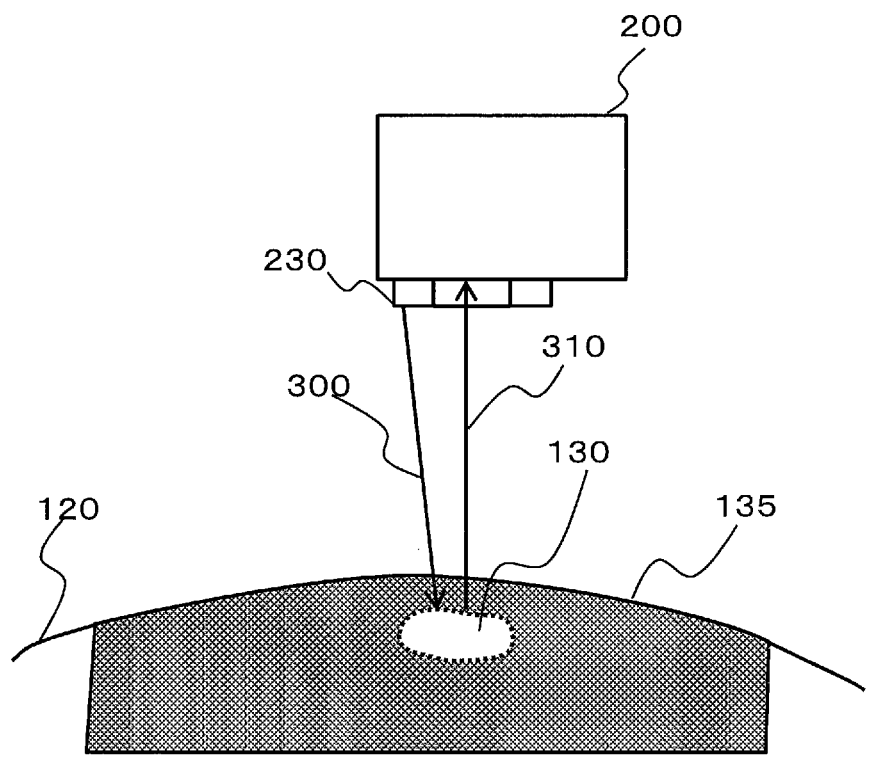
FIG. 4A is a view illustrating a state of a surgical field before projection in the surgery supporting system.
Figure 4B:
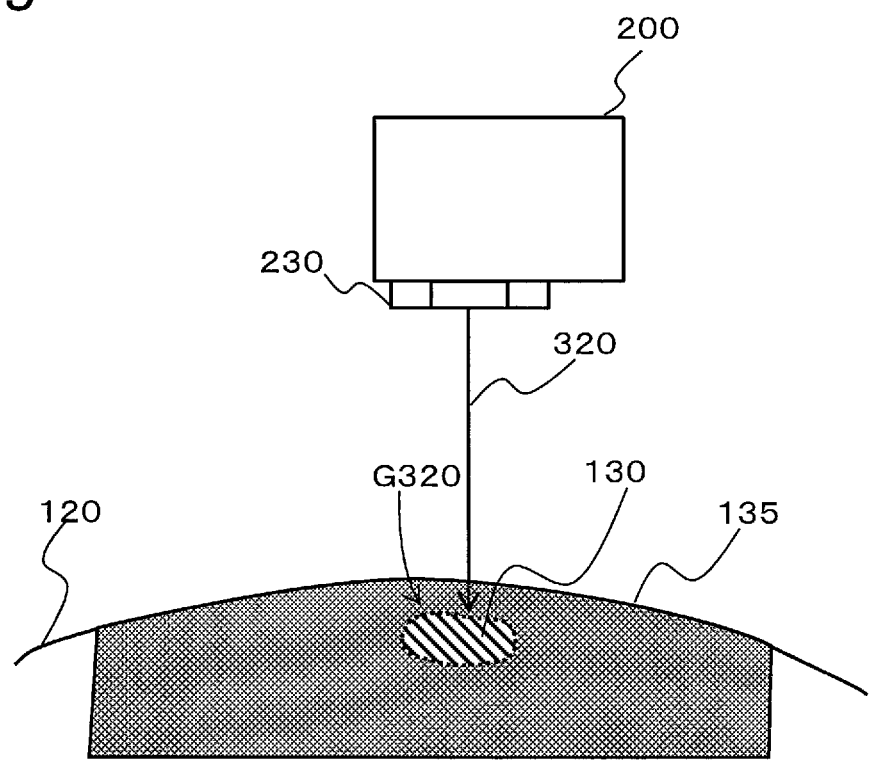

In the flowchart of FIG. 3, first, the projection control device 250 drives the excitation light source 230 to irradiate the surgical field 135 with the excitation light 300 as shown in FIG. 4A (S1). The irradiation of the excitation light 300 causes the affected part 130 in the surgical field 135 to emit fluorescence, and the fluorescence light 310 from the affected part 130 to be incident on the imaging irradiation device 200.

In the imaging irradiation device 200, as shown in FIG. 2, the fluorescence light 310 passes through the optical unit 201 and passes through the optical filter 213 of the camera 210. This allows the camera 210 to receive the fluorescence light 310 on the image pickup element 211.

Next, the projection control device 250 controls the camera 210, for example, to capture an image of the surgical field 135, and acquires the capture image from the camera 210 (S2). The capture image acquired in step S2 includes a fluorescence portion generated by receiving the fluorescence light 310 emitted by the affected part 130.

Next, the projection control device 250 performs image processing for generating a projection image based on the acquired capture image (S3). The projection control device 250 generates an image corresponding to the fluorescence portion in the capture image, and outputs the image to the projector 220 as a video signal.

In the image processing of step S3, for example, the projection control device 250 performs binarization on distribution of received light intensity in the capture image on the basis of a predetermined threshold value, to identify a region considered as a region of the fluorescence portion in the capture image. Subsequently, the projection control device 250, referring to various parameters stored in the memory 240, performs coordinate transformation such as shift, rotation, and enlargement/reduction on the image including the identified region, and correction of image distortion and the like. This results in generation of an image representing a specific region corresponding to the fluorescence portion in the capture image.

Next, the projection control device 250 controls the projector 220 so as to project a projection image based on the generated video signal (S4). By the control of the projection control device 250 causes, the projector 220 forms an image corresponding to the video signal from the projection control device 250 on the image formation surface of the image forming unit 222. The projector 220 drives the projection light source 221 to generate the projection light 315 representing the image on the image formation surface with visible light, and emits the projection light 315 to the optical unit 201 via the projection optical system 223 (see FIG. 2).

As shown in FIG. 2, the optical unit 201 reflects the projection light 315, which is visible light, and emits the projection light 320 along the optical axis J1. As a result, as shown in FIG. 4B, the imaging irradiation device 200 emits the projection light 320 to the surgical field 135, and a projection image G320 is projected onto the affected part 130 in the surgical field 135. The projection image G320 is, for example, a monochrome image.

The processing above is repeatedly executed at a predetermined cycle (e.g., $\frac{1}{60}$ to $\frac{1}{30}$ seconds).

Through the above processing, the projection control device 250 identifies the region of the affected part 130 emitting fluorescence on the basis of the capture image by the camera 210, and the projection image G320 of visible light is projected from the projector 220 onto the affected part 130. This enables, in the surgery supporting system 100, visualization of the affected part 130 that is difficult to visually recognize in visual inspection. The surgery supporting system 100 allows a doctor or the like to visually recognize a state of the affected part 130 in real time.

In the above description, a description has been given to an example in which the projection image G320 is a monochrome image. The projection control device 250 may generate a multi-gradation projection image by, for example, using a plurality of threshold values to determine a region of a fluorescence portion in a capture image in multiple stages. In addition, the projection control device 250 may generate a projection image so as to continuously reproduce the distribution of received light intensity in a capture image. Further, the projection image may be generated in plural colors or in full color. Various kinds of such setting of the projection image are adjusted by the user before execution of the normal mode, for example.

2-2. Adjustment Mode

Hereinafter, an adjustment mode in the surgery supporting system 100 according to the present embodiment will be described. The adjustment mode is an operation mode for adjusting various kinds of setting related to a projection image based on a capture image during execution of the normal mode.

2-2-1. Outline of Operation

An outline of an operation of the adjustment mode in the surgery supporting system 100 will be described with reference to FIGS. 5A and 5B.

Figure 5A:
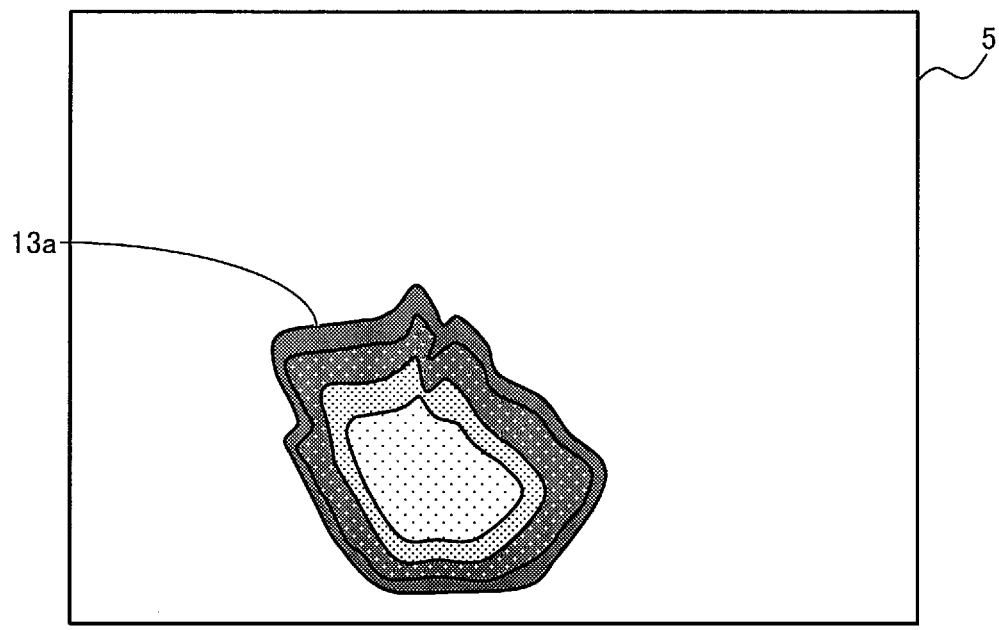
FIG. 5A is a view illustrating image data of a fluorescence image in the surgery supporting system.
Figure 5B:
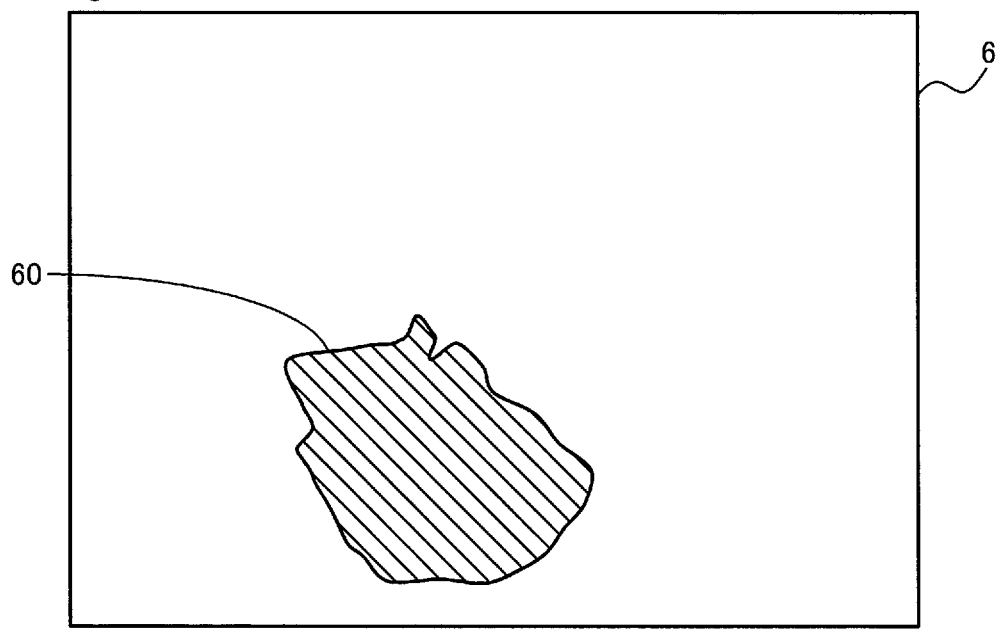
FIG. 5B is a view illustrating image data of a projection image based on the fluorescence image of FIG. 5A.

FIG. 5A illustrates image data of a fluorescence image 5 in the surgery supporting system 100. FIG. 5B illustrates image data of a projection image 6 generated on the basis of the fluorescence image 5 of FIG. 5A. The fluorescence image 5 is a capture image obtained by capturing a fluorescence portion 13a based on fluorescence emission in a human body such as an organ 13 (see FIG. 7C) with the camera 210, while blocking a reception of light other than fluorescence light (e.g., visible light, excitation light, and the like).

In the normal mode of the surgery supporting system 100, the projection image 6 (FIG. 5B) is generated (S3 of FIG. 3) by performing, as described above, the binarization or the like for noise removal on the fluorescence image 5 as shown in FIG. 5A, and the projection image 6 is projected onto the human body such as the organ 13. As a method of adjusting a threshold value of the binarization or the like, a method can be considered in which, for example, while the projection image 6 is projected onto the human body, the fluorescence image 5 to be a base for generation of the projection image 6 is displayed on the monitor 160 (FIG. 1).

However, in the above-described method for adjustment, the operator 140 (user) directs eyes to each of the projection image 6 projected on the human body and the fluorescence image 5 displayed on the monitor 160, and adjusts the threshold value and the like while comparing the images.

That is, in adjusting the projection image 6, it is necessary to move the eyes between the projected portion on the human body and the monitor 160.

To solve this problem, in the adjustment mode of the present embodiment, the projection image 6 to be adjusted and the fluorescence image 5 for generation of the projection image 6 are coaxially superposed with each other and displayed. This can omit movement of the eyes for comparing the projection image 6 and the fluorescence image 5 in adjusting the projection image 6, and facilitate adjustment related to the projection image 6.

Further, in the present embodiment, by transmitting and displaying the images superimposed in the adjustment mode, or superimposing the image on an object to be imaged such as the organ 13 (see FIGS. 7A to 7C), a relationship between the projection image 6 being adjusted and the fluorescence image 5 or the organ 13 can be easily confirmed. Hereinafter, an operation of the surgery supporting system 100 in the adjustment mode of the present embodiment will be described in detail.

2-2-2. Adjustment Mode Operation

Figure 6:
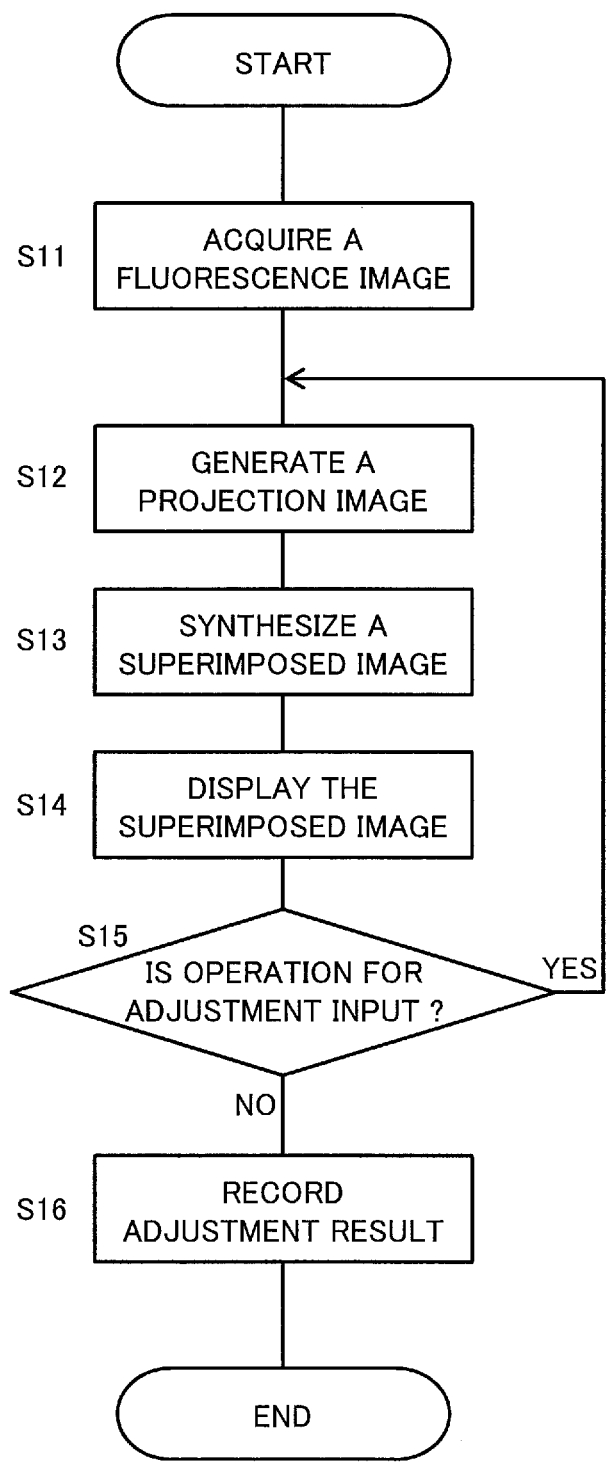
FIG. 6 is a flowchart for explaining an operation in an adjustment mode in the surgery supporting system.

An operation of the adjustment mode in the surgery supporting system 100 will be described with reference to FIGS. 6 to 8B. FIG. 6 is a flowchart for explaining an operation of the adjustment mode in the surgery supporting system 100.

The flowchart of FIG. 6 is executed by the projection control device 250 in a state where various parameters for executing the image processing (S3 in FIG. 3) in the normal mode before adjustment are stored in advance in the memory 240, for example. The processing according to this flowchart is started, for example, when the user performs an operation indicating a start of the adjustment mode via the mouse 170.

First, the projection control device 250 controls the excitation light source 230 and the camera 210 similarly to the normal mode (S1 and S2 in FIG. 3) to acquire image data of the fluorescence image 5 in FIG. 5A from the camera 210 (S11) for example. The fluorescence image 5 in FIG. 5A includes luminance distribution of fluorescence emission in the fluorescence portion 13a of the organ 13. Imaging and acquisition of the fluorescence image 5 is repeatedly performed at a predetermined cycle (e.g., 1/60 to 1/30 seconds).

Figure 7A:
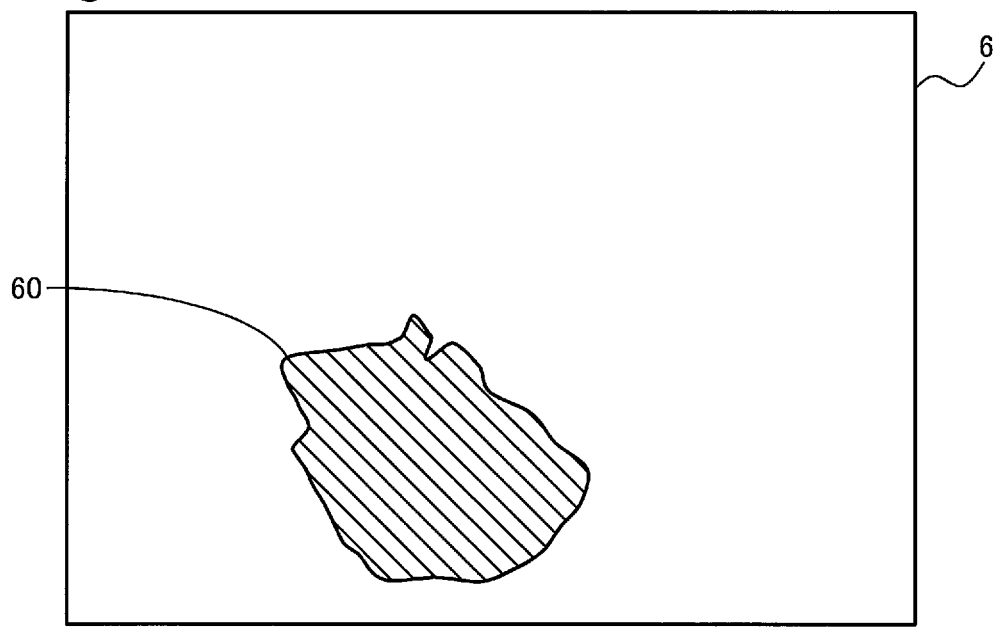
FIG. 7A is a view illustrating image data of a projection image in the adjustment mode.

Next, on the basis of the acquired fluorescence image 5, the projection control device 250 performs the image processing (S3 in FIG. 3) for generating a projection image similar to that in the normal mode (S12). FIG. 7A illustrates image data of the projection image 6 generated in step S12.

The image data of the example of FIG. 7A shows the projection image 6 generated on the basis of the fluorescence image 5 of FIG. 5A, and includes a monochrome projection area 60. The projection area 60 corresponds to a region of a pixel having a luminance equal to or higher than a specific threshold value in the fluorescence image 5 of FIG. 5A. For example, the projection control device 250 compares the threshold value previously recorded in the memory 240 with a luminance for each pixel of the fluorescence image 5, and performs binarization to generate the image data of FIG. 7A.

Figure 7B:
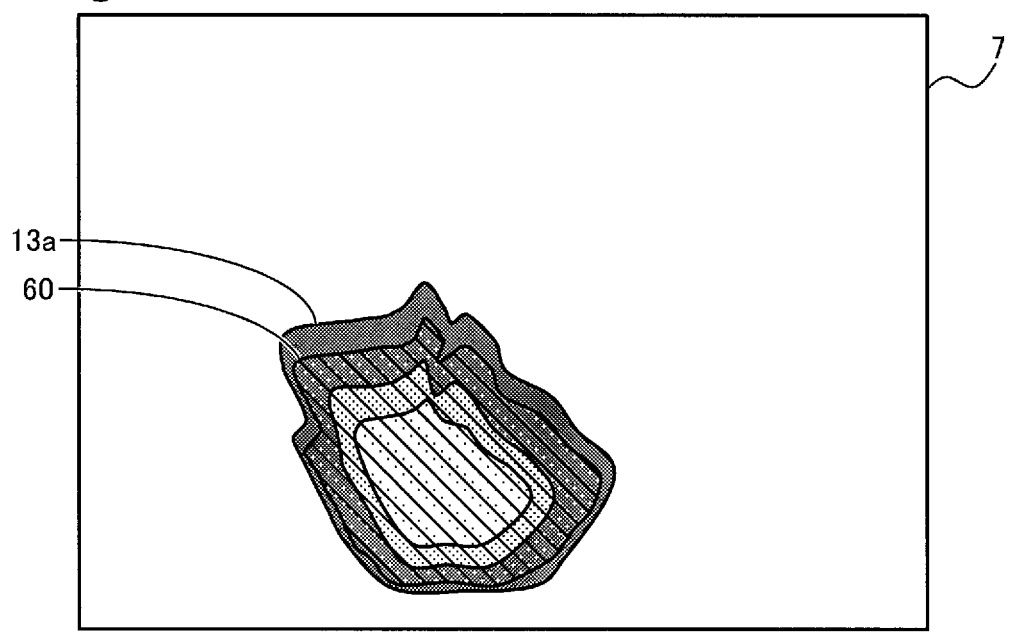
FIG. 7B is a view illustrating image data of a superimposed image in the adjustment mode.

Next, the projection control device 250 performs image synthesis for a superimposed image on the basis of image data of the acquired fluorescence image 5 and the generated projection image 6 (S13). The superimposed image is an image in which the fluorescence image 5 and the projection image 6 are superimposed with each other at a position corresponding before and after the image processing (S12). FIG. 7B illustrates image data of a superimposed image 7 synthesized in step S13.

The image data of the superimposed image 7 in FIG. 7B has a superimposition order in which the projection image 6 in FIG. 7A is superimposed over the fluorescence image 5 in FIG. 5A. Here, the superimposition order among the images represents an order in which the individual images 5 and 6 before synthesis are preferentially displayed on the superimposed image 7 of the synthesis result. For example, in the superimposed image 7 in FIG. 7B, the above order gives priority to display of the projection area 60 over the corresponding region of the fluorescence image 5.

In step S13, the projection control device 250 synthesizes the superimposed image 7 so as to transmit the superimposition of the fluorescence image 5 and the projection image 6 by an alpha blending method, for example. Various values can be set for a transmittance among the images. For example, by setting a transmittance of the image having an upper superimposition order to be 50%, the image of a lower order is transmitted by 50%. Further, for a colorless region (see FIG. 7A) in the image of the upper order, such as a region other than the projection area 60 in the superimposed image 7 in FIG. 7B, the lower image is exposed. The projection control device 250 synthesizes the superimposed image 7 of FIG. 7B on the basis of the superimposition order and a transmittance recorded in the memory 240 in advance.

Figure 7C:
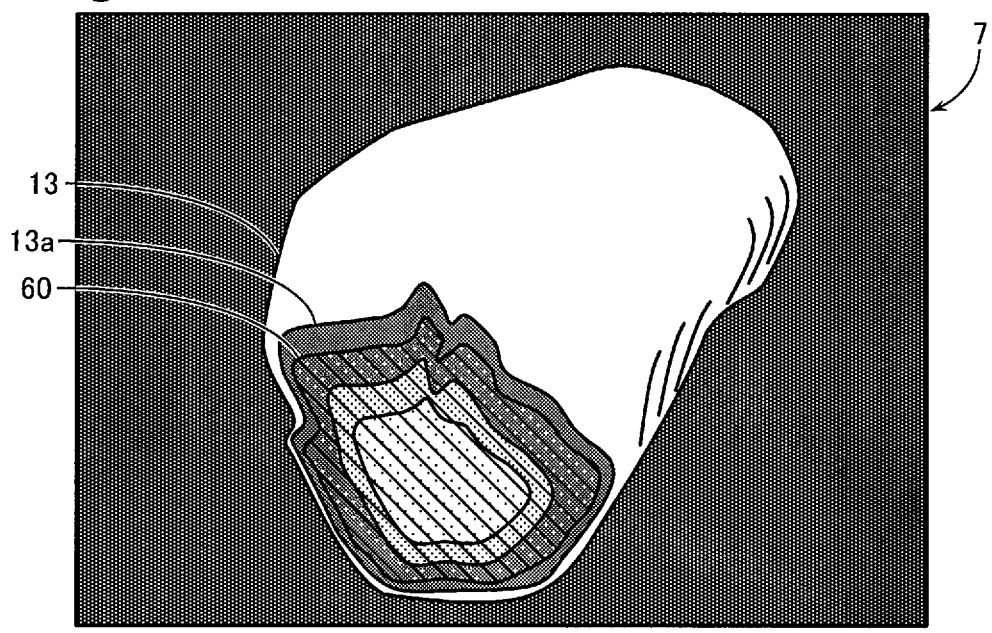
FIG. 7C is a view showing a display example of a superimposed image in the adjustment mode.

Returning to FIG. 6, next, the projection control device 250 outputs a video signal indicating image data to the projector 220 on the basis of the image data of the synthesized superimposed image 7, and displays the superimposed image 7 by projection (S14). FIG. 7C shows a display example of the superimposed image 7 displayed on the organ 13 by the projection in step S14.

As shown in FIG. 7C, the superimposed image 7 is projected onto the actual organ 13 by projection from the projector 220. This allows the fluorescence image 5 and the projection image 6 to be preferentially displayed rather than the organ 13. Further, the projection image 6 in the superimposed image 7 in FIG. 7C is transmitted through the fluorescence image 5. Such projection display of the superimposed image 7 enables the user to confirm a range of luminance distribution of the fluorescence image 5 where the projection area 60 is superimposed, a state of the organ 13, and the like at a glance without moving the eyes.

The surgery supporting system 100 in the adjustment mode receives a user operation (S14), for example, in a state where the superimposed image 7 is displayed as shown in FIG. 7C. For example, the user uses the mouse 170 of the display control device 150 (FIG. 1) to input an operation for performing various kinds of adjustment on the superimposed image 7 being displayed. The display control device 150 transmits an instruction indicating the input operation contents to the projection control device 250.

Figure 8A:
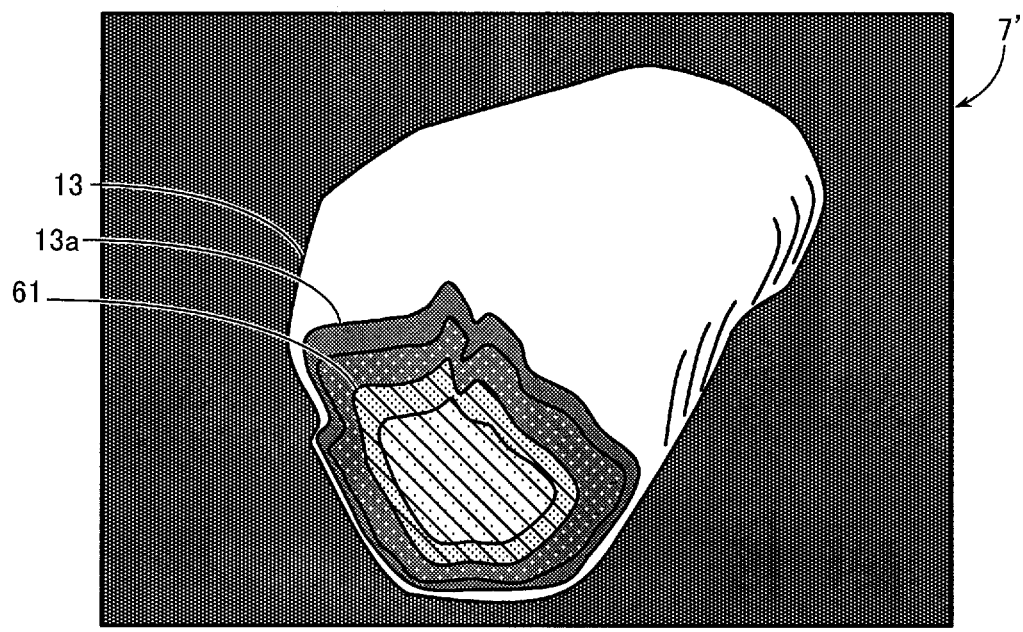
FIG. 8A is a view showing a display example of a superimposed image updated from FIG. 7C.

On the basis of the instruction from the display control device 150, the projection control device 250 determines whether or not the input operation is an operation for adjustment on the superimposed image 7 (S15). When determining that the input operation is the operation for adjustment (YES in S15), the projection control device 250 adjusts various parameters in accordance with the operation contents, and performs processing in and after step S12 by using the adjusted parameters. This causes update of the superimposed image 7 displayed in step S14. FIG. 8A shows a display example of a superimposed image 7' updated from the superimposed image 7 shown in FIG. 7C.

FIG. 8A shows an example of changing the threshold value used for generating projection image 6 in FIG. 7A. For example, when the user performs an operation to raise (or lower) the threshold value, the projection control device 250 proceeds to "YES" in step S15. In the subsequent step S12, the projection control device 250 performs image processing such as binarization by using the raised (or lowered) threshold value, and displays a superimposed image 7' including a new projection area 61 as shown in FIG. 8A, in a step S14.

The projection area 61 in FIG. 8A is smaller than the projection area 60 in FIG. 7C in response to an increase of the threshold value. According to the superimposed images 7 and 7' of FIGS. 7C and 8A, the user can adjust the threshold value while simultaneously observing a change of a range of the projection areas 60 and 61 being adjusted and the fluorescence image 5 and the organ 13. For example, the user repeatedly adjusts the threshold value until the projection area 61 reaches a desired range (YES in S15), and inputs an operation indicating completion of the adjustment when finding an appropriate threshold value.

Returning to FIG. 6, when the operation for adjustment completion is input, the projection control device 250 determines that the input operation is not an operation for adjustment (NO in S15), and records the adjustment result (S16). This processing is for performing setting preservation for reproducing, in the normal mode, a projection image 6' adjusted in the adjustment mode (see FIGS. 8A and 8B). For example, the projection control device 250 records, in the memory 240, various parameters used in the image processing of step S12 for generating the superimposed image 7' being displayed.

The projection control device 250 records the adjustment result in step S16, thereby ending the processing according to this flowchart.

Figure 8B:
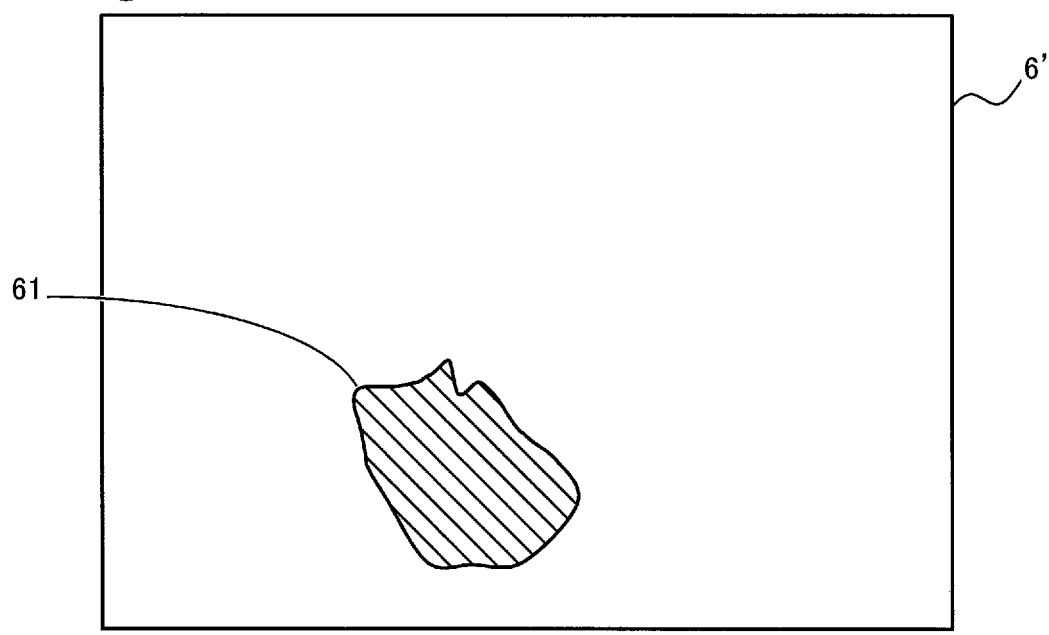
FIG. 8B is a view illustrating image data of a projection image after adjustment in FIG. 8A.

According to the above processing, in the superimposed image 7 (FIG. 7C) during the adjustment mode of the surgery supporting system 100, the fluorescence image 5 (FIG. 5A) and the projection image 6 (FIG. 7A) based on the fluorescence image 5 are coaxially superimposed and displayed on the actual organ 13 (S14). This makes it easier for the user to adjust the projection image 6 while confirming the fluorescence image 5 and a state of the organ 13. FIG. 8B illustrates image data of the projection image 6' after adjustment in the adjustment mode.

FIG. 8B shows the projection image 6' in the normal mode executed after adjustment of the example of FIG. 8A. Upon execution of the normal mode after adjustment, the projection control device 250 performs the image processing (S3 in FIG. 3) for generating the projection image 6' by using various parameters recorded in the memory 240 in step S16 of FIG. 6. This causes, as shown in FIG. 8B, the projection area 61 included in the superimposed image 7' (FIG. 8A) at the time of the adjustment to be reproduced in the projection image 6' projected in the normal mode. Thus, the user can use the projection image 6' subjected to the desired adjustment, in the normal mode.

2-2-3. Example of Operation in Adjustment Mode

In the above description, a description has been given to an example of adjusting the binarization threshold value, with reference to FIGS. 8A and 8B. In the adjustment mode of the surgery supporting system 100, various kinds of adjustment can be made without limiting to the threshold value. Hereinafter, operation examples in the adjustment mode of the surgery supporting system 100 will be described.

(1) Adjustment of Projection Image

Figure 9A:
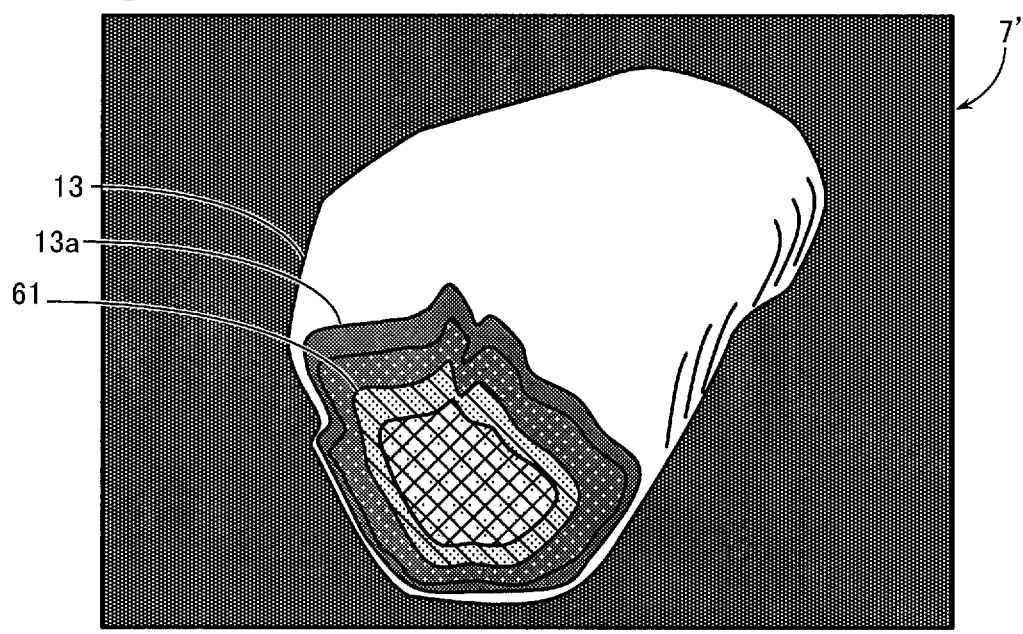
FIG. 9A is a view showing a display example of a superimposed image upon gradation adjustment.
Figure 9B:
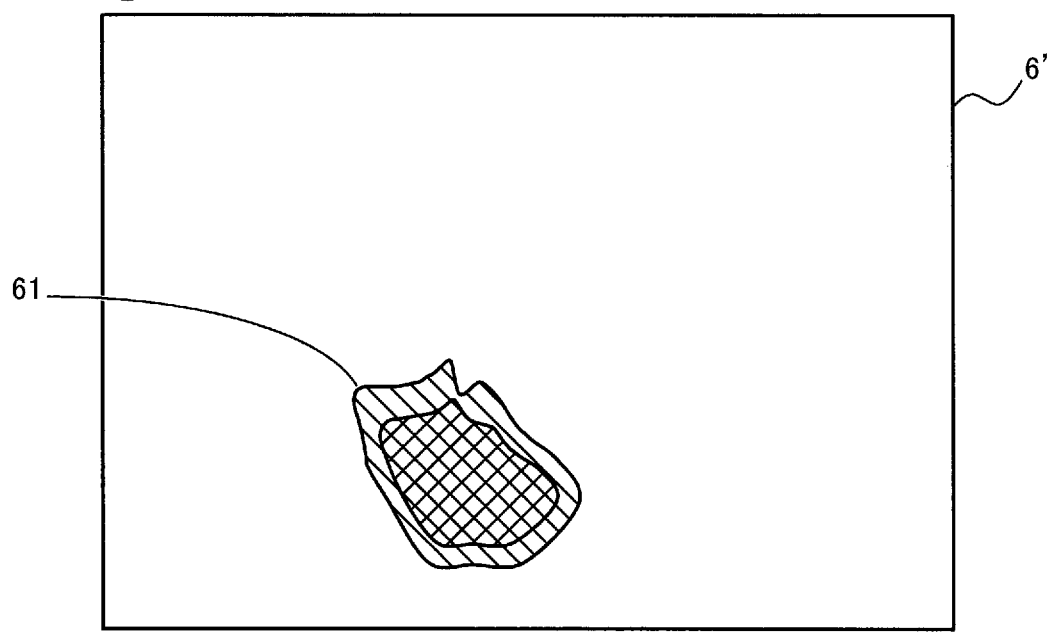
FIG. 9B is a view illustrating image data of a projection image after adjustment in FIG. 9A.

In the adjustment mode of the surgery supporting system 100, gradation adjustment on the projection image 6' may be performed. FIG. 9A shows a display example of the superimposed image 7' upon gradation adjustment. FIG. 9B illustrates image data of the projection image 6' after adjustment according to FIG. 9A.

FIGS. 9A and 9B show the example of achieving a higher gradation from the projection image 6' in FIG. 8B. For example, when the user specifies a desired gradation number such as four gradations, eight gradations, and the like (YES in S15), the projection control device 250 performs image processing including multi-value conversion (four-value conversion, eight-value conversion, and the like) in accordance with the specified gradation number (S12). This causes update of display of the superimposed image 7' from FIG. 8A to FIG. 9A (S14). In the superimposed image 7' of FIG. 9A, the projection area 61 has a plurality of gradations. In the adjustment mode, threshold value adjustment or the like for each gradation may be performed.

Saving the adjustment result by the superimposed image 7' in FIG. 9A (S16) causes, in the subsequent normal mode, the projection image 6' colored with a gradation similar to that of the projection area 61 in FIG. 9A to be projected as shown in FIG. 9B. Thus, a higher gradation of the projection image 6' is achieved from FIG. 8B to FIG. 9B. Also, a lower gradation of the projection image 6' can be achieved similarly to the above.

Figure 10A:
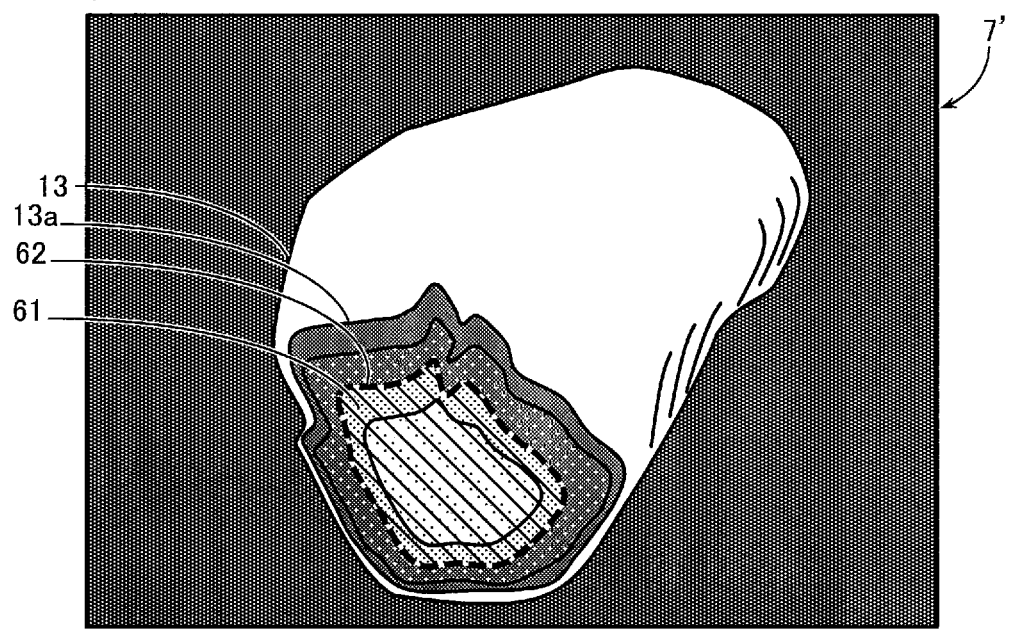
FIG. 10A is a view showing a first display example of a superimposed image upon boundary line adjustment.
Figure 10B:
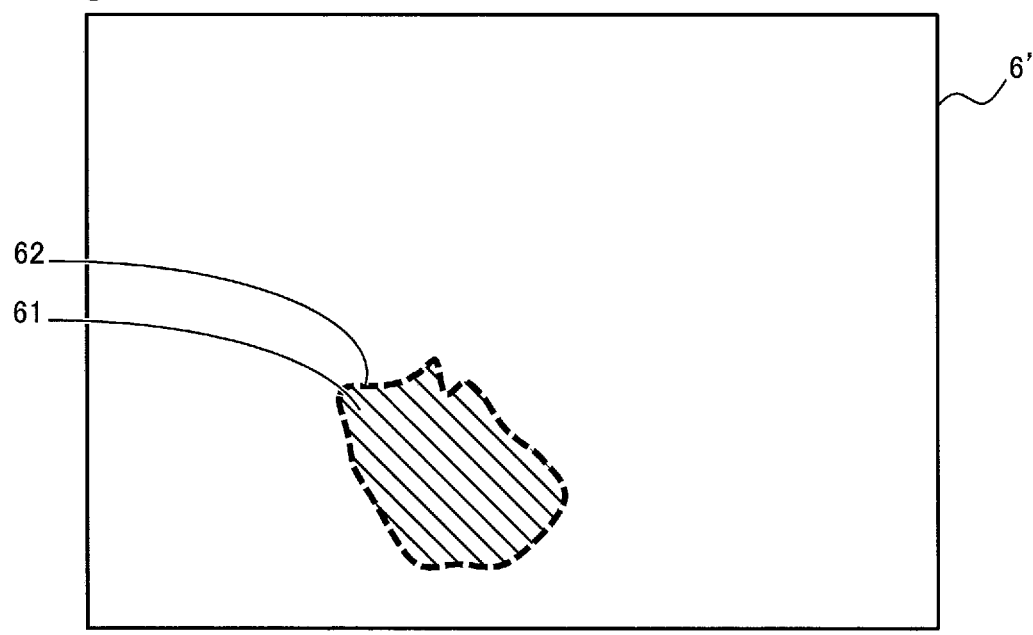
FIG. 10B is a view illustrating image data of a projection image after adjustment in FIG. 10A.

In the adjustment mode, a boundary line in the projection image 6 may be adjusted in order to use the boundary line as a cutting line indicating a cutting position of a surgical operation, for example. FIG. 10A shows a first display example of the superimposed image 7' upon boundary line adjustment. FIG. 10B illustrates image data of the projection image 6' after adjustment in FIG. 10A.

FIGS. 10A and 10B show the example of adding a boundary line to the projection image 6' of FIG. 8B. In this case, in the image processing of step S12, the projection control device 250 performs boundary extraction processing on the binarized or multi-valued image, and draws a boundary line 62 around the projection area 61. This causes the boundary line 62 to be added to the superimposed image 7 in FIG. 8A as shown in FIG. 10A, in the subsequent step S14. By saving such an adjustment result (S16), the boundary line 62 is added to the projection image 6' in FIG. 8B as shown in FIG. 10B, in the subsequent normal mode.

Figure 11A:
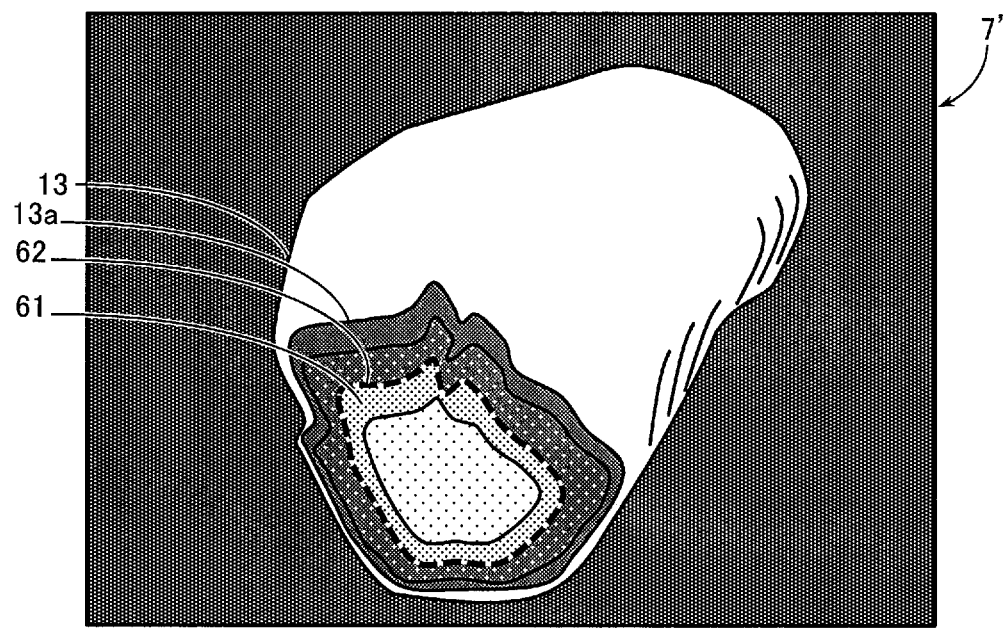
FIG. 11A is a view showing a second display example of a superimposed image upon boundary line adjustment.
Figure 11B:
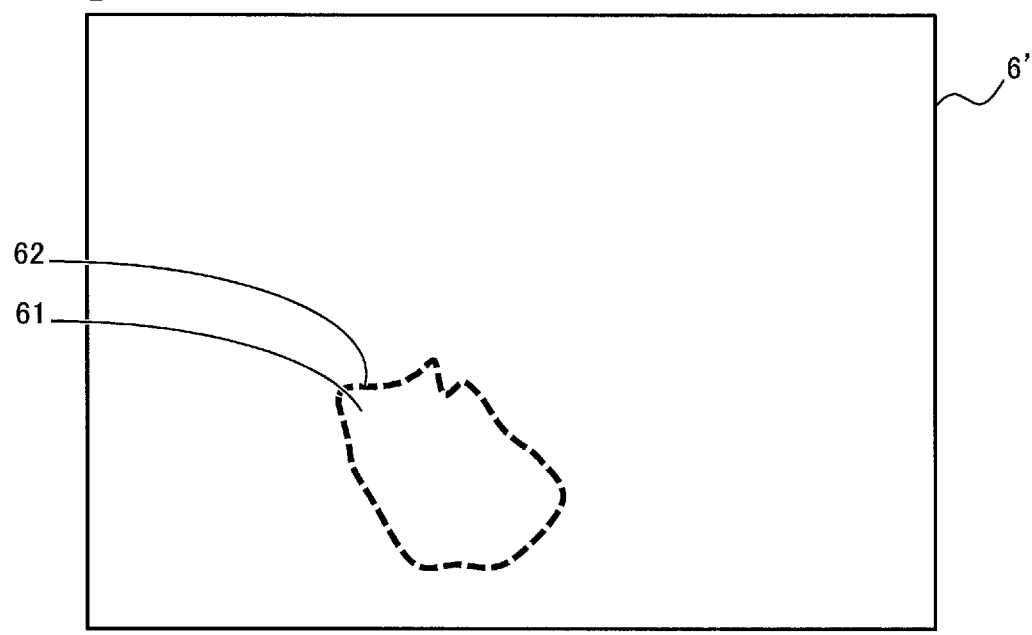
FIG. 11B is a view illustrating image data of a projection image after adjustment in FIG. 11A.

In the above example (FIGS. 10A and 10B), the boundary line 62 is added to the projection image 6' (FIG. 8B), but adjustment may be performed so as to project the boundary line 62 alone in the normal mode. FIG. 11A shows a second display example of the superimposed image 7' upon boundary line adjustment. FIG. 11B illustrates image data of the projection image 6' after adjustment in FIG. 11A.

For example, in the image processing of step S12, the projection control device 250 omits coloring inside the projection area 61 on the basis of specification by the user (FIG. 11A). According to the adjustment result of FIG. 11A, the projection image 6' of the boundary line 62 alone is projected in the subsequent normal mode as shown in FIG. 11B.

Further, for the adjustment of the boundary line 62 in the projection image 6', for example, a projected position of the boundary line 62 in the projection image 6' may be adjusted so as to be located at a position apart from the actual boundary position by a predetermined interval.

In addition, in the adjustment mode, adjustment may be performed such that various kinds of additional information such as text information and image information are projected in the normal mode. Further, sensitivity or the like of the fluorescence image 5 to be a base of the projection image 6 may be adjusted. Furthermore, a light amount, level, and the like of the projection image 6 may be adjusted.

(2) Display Adjustment of Superimposed Image

In order to facilitate adjustment of the projection image 6 or the like in the normal mode as described above, display of the superimposed image 7 itself may be adjusted in the adjustment mode according to the present embodiment. Hereinafter, an operation example of display adjustment of the superimposed image 7 will be described with reference to FIGS. 12A and 12B.

Figure 12A:
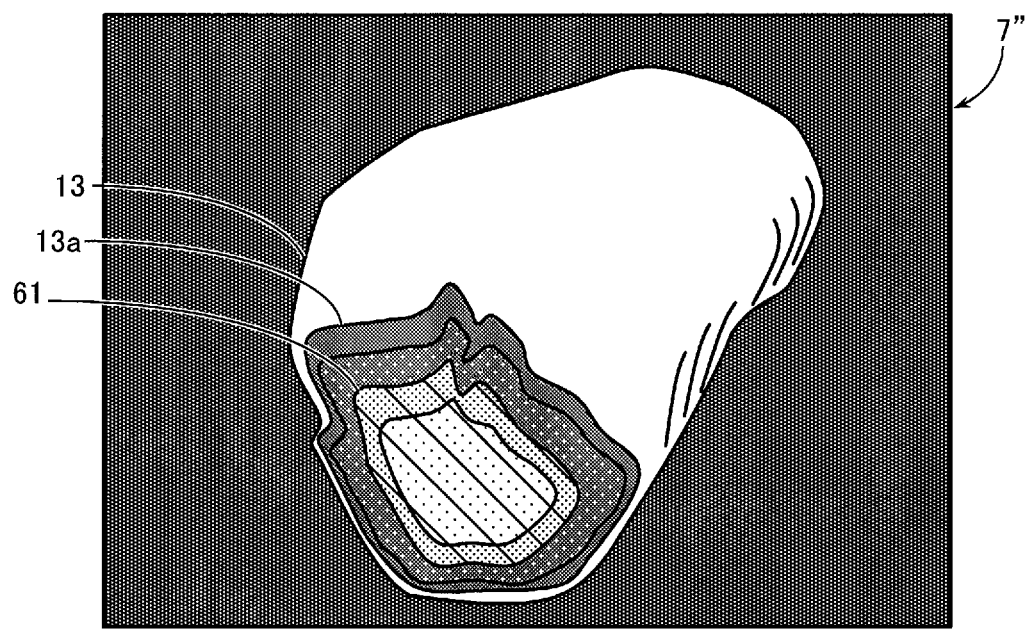
FIG. 12A is a view showing a first display example in display adjustment of a superimposed image.
Figure 12B:
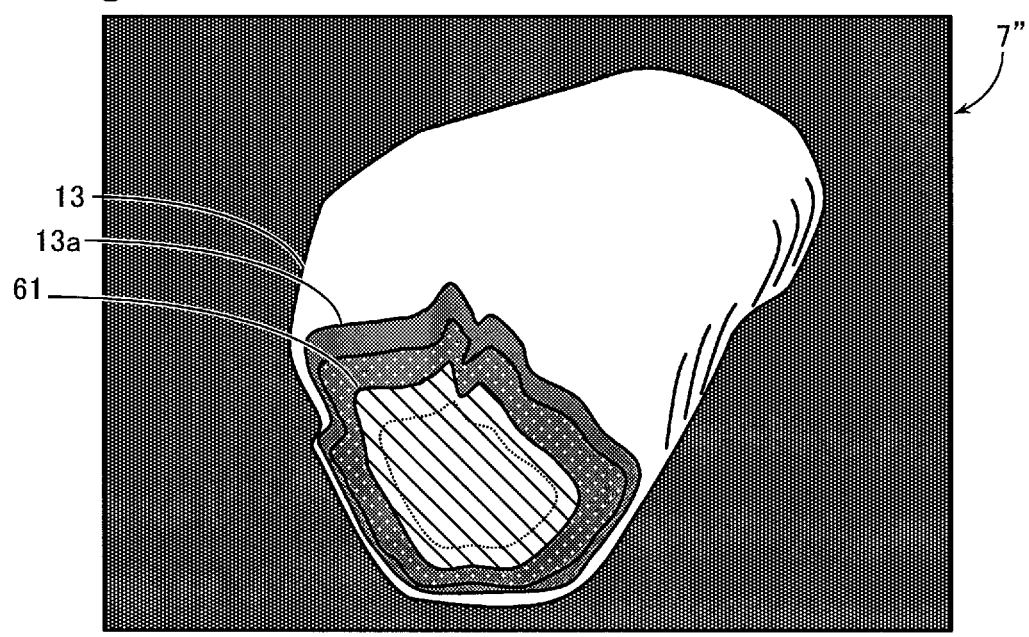
FIG. 12B is a view showing a second display example in display adjustment of a superimposed image.

FIG. 12A shows a first display example of the superimposed image 7" subjected to display adjustment. FIG. 12B shows a second display example in the display adjustment of the superimposed image 7" subjected to the display adjustment.

For example, as the display adjustment of the superimposed image 7", the transmittance among images superimposed in the superimposed image 7" may be changed. For example, by the user specifying a desired transmittance through the mouse 170 (YES in S15), the projection control device 250 synthesizes the superimposed image 7" by using the specified transmittance, in image synthesis of the subsequent step S13.

FIG. 12A illustrates the superimposed image 7" in a case where the transmittance of the projection image 6' (projection area 61) is adjusted to be higher from the superimposed image 7' of FIG. 8A. As shown in FIG. 12A, by adjusting the transmittance to a higher transmittance, display of the projection area 61 becomes lighter in the superimposed image 7", and display of luminance distribution of the corresponding fluorescence image 5 becomes darker. This makes it easier to see a state such as luminance distribution of the fluorescence image 5 inside the projection area 61, and can facilitate adjustment of the threshold value and the like for binarization or multi-value conversion, for example.

FIG. 12B illustrates a case where the transmittance of the projection image 6' is adjusted to be lower from the superimposed image 7' of FIG. 8A. As shown in FIG. 12B, by adjusting the transmittance to a lower transmittance as shown in FIG. 12B, display of the projection area 61 in the superimposed image 7" can be brought close to the projected state in the normal mode (see FIG. 8B). Therefore, for example, adjustment of the light amount, level, and the like of the projection image 6' can be facilitated.

The transmittance in the superimposed image 7" can be set for each of the projection image 6' and the fluorescence image 5, for example. Each transmittance may be changed as appropriate within a range of 0 to 100%. Further, in a case where the transmittance of the projection image 6' is 0%, display of the fluorescence image 5 superimposed on the projection area 61 may be omitted. Further, the transmittance of the projection image 6' and the fluorescence image 5 as a whole may be changed.

The display adjustment of the superimposed image 7" is not limited to the change of the transmittance. For example, adjustment may be performed to switch the superimposition order of the images in the superimposed image 7". For example, when the user performs an operation for switching the order through the mouse 170 (YES in S15), the projection control device 250 synthesizes the superimposed image 7" in accordance with the switched order, in the subsequent step S13. This can facilitate confirmation of a correspondence between the fluorescence image 5 and the projection image 6.

2-2-4. Adjustment Mode by Monitor Display

In the above description, the superimposed image 7 is projected from the projector 220 in the adjustment mode of the surgery supporting system 100. However, the superimposed image 7 may be displayed on the monitor 160 (see FIG. 1). The adjustment mode by monitor display will be described with reference to FIGS. 13A to 13D.

Figure 13A:
FIG. 13A is a view illustrating image data of an object image in an adjustment mode by monitor display.
Figure 13B:
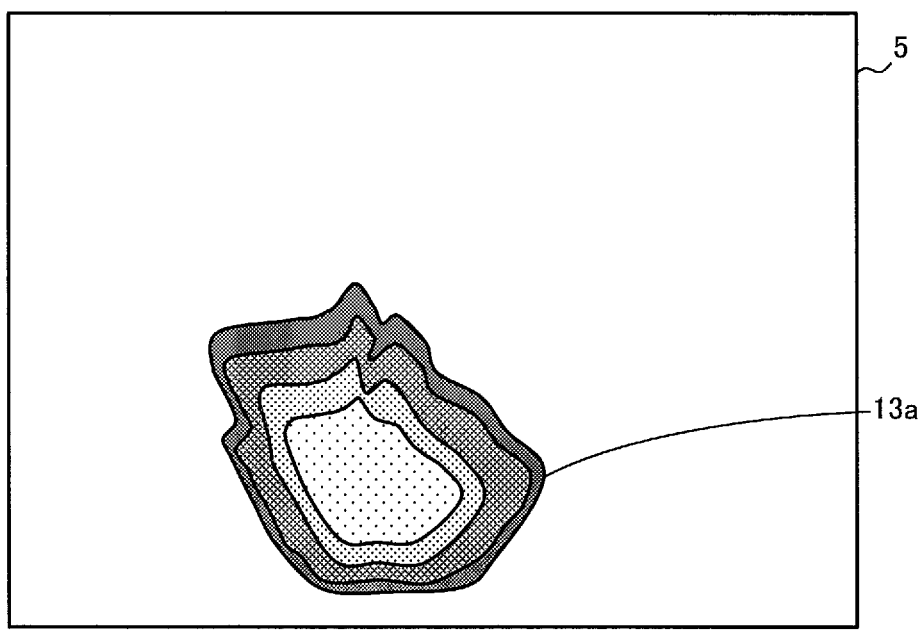
FIG. 13B is a view illustrating image data of a fluorescence image in the adjustment mode by monitor display.
Figure 13C:
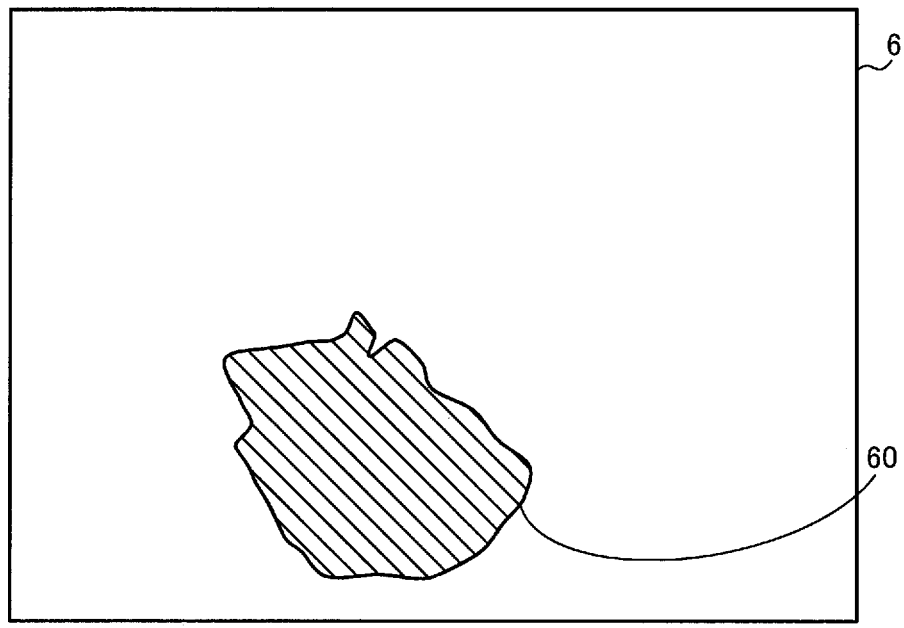
FIG. 13C is a view illustrating image data of a projection image in the adjustment mode by monitor display.
Figure 13D:
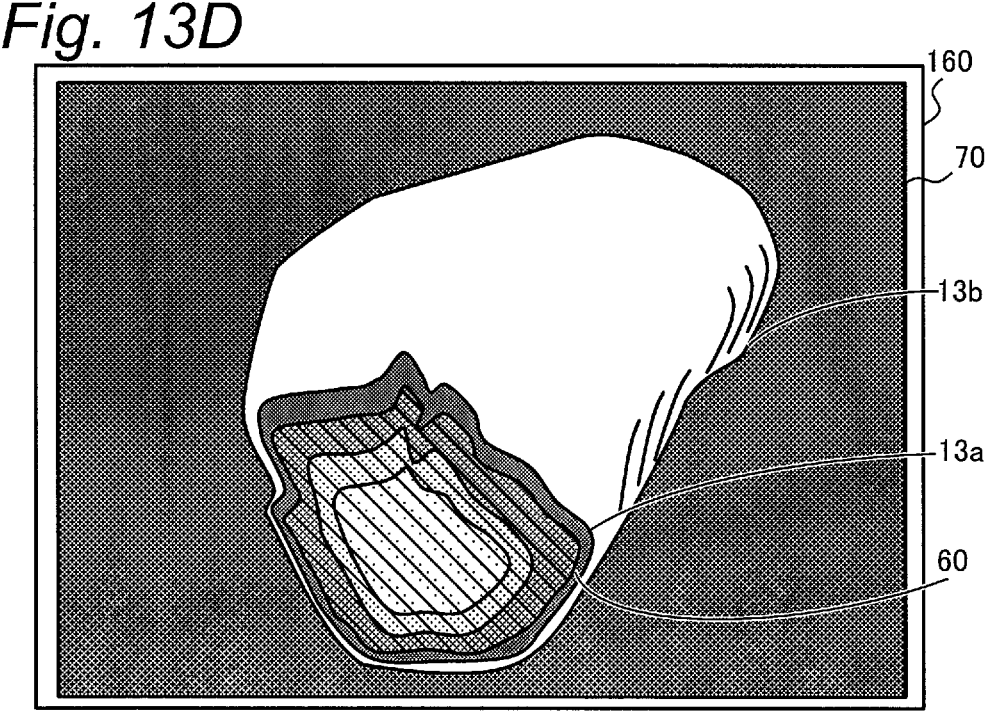
FIG. 13D is a view showing a display example of a superimposed image in the adjustment mode by monitor display.

FIG. 13A is an example of image data of an object image 8 in the adjustment mode by monitor display. FIG. 13B is an example of image data of the fluorescence image 5. FIG. 13C is an example of image data of the projection image 6. FIG. 13D is a display example of a superimposed image 70 on the monitor 160.

Upon executing the adjustment mode by monitor display, the camera 210 (FIG. 1) captures the object image 8 with visible light, excitation light (infrared light), or the like in a time-division manner from the capturing of the fluorescence image 5, for example, by switching control of the filter mechanism of the optical filter 213 (FIG. 2). In this case, the optical unit 201 is configured to transmit a part of visible light. The object image 8 is an image representing an outer shape and the like of an object in the surgery supporting system 100. The object image 8 in FIG. 13A includes an organ image 13*b* with the organ 13 as the object (see FIG. 5B).

In the adjustment mode by monitor display, for example, the display control device 150 executes processing similar to that in the flowchart of FIG. 6. In step S11 of FIG. 6, the display control device 150 acquires, from the camera 210, the fluorescence image 5 (FIG. 13B) and acquires the object image 8 (FIG. 13A).

Next, on the basis of the acquired fluorescence image 5 (FIG. 13B), the display control device 150 executes image processing (S12) similar to that of the projection control device 250, for example, to generate image data of the projection image 6 as shown in FIG. 13C. Next, the display control device 150 synthesizes the superimposed image 70 on the basis of the image data of the object image 8, the fluorescence image 5, and the projection image 6 (S13), and displays the superimposed image 70 synthesized as shown in FIG. 13D on the monitor 160 (S14).

In the adjustment mode by monitor display, as shown in FIG. 13D, three pieces of image data, such as the object image 8 (FIG. 13A), the fluorescence image 5 (FIG. 13B), and the projection image 6 (FIG. 13C), are superimposed in the superimposed image 70. This enables continuation of a positional relationship between the organ image 13*b* and the projection area 60 on the monitor 160, and can facilitate various kinds of adjustment. In a case where adjustment can be performed by confirming the fluorescence image 5 and the projection image 6, the object image 8 may be omitted from the superimposed image 70 displayed on the monitor 160.

In the superimposed image 70 of FIG. 13D, the superimposition order of the images is set to the order of, from the top, the projection image 6 (FIG. 13C), the fluorescence image 5 (FIG. 13B), and the object image 8 (FIG. 13A), for example. As a result, the projection image 6 can be preferentially displayed rather than the fluorescence image 5 and the object image 8. The transmittance and the superimposition order among the images can be appropriately adjusted by a user operation, similarly to the case of the adjustment mode by the projector 220 described above. Note that the transmittance of the image displayed at the lowest (the object image 8 in FIG. 13D) may be 0% (not transmitted) and the transmittance of other images may be adjusted.

3. Effects and Others

As described above, in the present embodiment, the surgery supporting system 100 includes the excitation light source 230, the camera 210, the projection control device 250, the projector 220, and the mouse 170. The excitation light source 230 emits excitation light of a predetermined wavelength to an object such as the organ 13. The camera 210 captures the fluorescence image 5 based on the fluorescence excited by the excitation light. The projection control device 250 generates the projection image 6 based on the fluorescence image 5 captured by the camera 210. The projector 220 displays the projection image 6. The mouse 170 adjusts the projection image 6 on the basis of a user operation. The projector 220 displays the superimposed image 7 in which the projection image 6 and the fluorescence image 5 are superimposed with each other, when the projection image 6 is adjusted by the mouse 170.

According to the above surgery supporting system 100, the projection image 6 and the fluorescence image 5 are superimposed with each other and displayed in the superimposed image 7. This can facilitate adjustment of various display images such as the projection image 6 displayed by the surgery supporting system 100.

In the present embodiment, the projection control device 250 generates the superimposed image 7 to transmit the superimposition of the fluorescence image 5 and the projection image 6. This enables visualization of the superimposition of the fluorescence image 5 and the projection image 6 in the superimposed image 7, and can facilitate various kinds of adjustment in the surgery supporting system 100.

In the present embodiment, the mouse 170 changes a transmittance among the images that are superimposed in the superimposed image 7, on the basis of a user operation. Thus, the user can adjust the transmittance to a desired transmittance, to make it easier to observe the superimposition of the images in the superimposed image 7.

In the present embodiment, the projector 220 constitutes a display that projects the superimposed image 7 onto an object such as the organ 13. This enables direct confirmation of a positional relationship of the actual object with the projection image 6 and the fluorescence image 5.

In the present embodiment, the monitor 160 may constitute a display having a display surface on which the superimposed image 70 is displayed. This allows the user to adjust the projection image 6 or the like without particularly moving the eyes from the monitor 160.

In the present embodiment, the camera 210 functions as an imager that captures the fluorescence image 5, and also functions as an object imager that captures the object image 8 representing an object. The superimposed image 70 displayed by the monitor 160 is an image in which the object image 8, the fluorescence image 5, and the projection image 6 are superimposed with each other. This enables confirmation, on the monitor 160, of a positional relationship of the object with the projection image 6 and the fluorescence image 5.

In the present embodiment, the display, which is the projector 220 or the monitor 160, preferentially displays the projection image 6 rather than the fluorescence image 5 in the superimposed images 7 and 70. This makes it easier for the user to visually recognize the projection image 6 to be adjusted.

In the present embodiment, on the basis of a user operation, the mouse 170 switches the order of the images superimposed in the superimposed image 7. This makes it possible to preferentially display images in the superimposed image 7 in the order desired by the user.

In the present embodiment, the mouse 170 adjust, on the basis of a user operation, at least one of the threshold value for generating the projection image 6 on the basis of the fluorescence image 5, the gradation of the projection image 6, or the boundary line of the projection image 6. Thus, various kinds of adjustment of the projection image 6 in the surgery supporting system 100 can be performed.

In the present embodiment, the surgery supporting system 100 further includes the memory 240 that records the adjustment result of the display image adjusted by the mouse 170. The projection control device 250 generates the projection image 6 based on the fluorescence image 5 with reference to the adjustment result recorded in the memory 240. This enables reproduction of the adjustment result in the adjustment mode, in the normal mode.

Other Embodiments

As described above, the first embodiment has been described as an example of the technique disclosed in the present application. However, the technique in the present disclosure is not limited to this, and can also be applied to embodiments in which change, replacement, addition, omission, and the like are made as appropriate. Further, it is also possible to combine each constituent element described in the first embodiment above, to provide a new embodiment.

Accordingly, other embodiments will be exemplified below.

In the first embodiment above, the surgery supporting system 100 that provides visual support with the projector 220 has been described. However, the display system according to the present disclosure is not limited to the surgery supporting system 100. A modified example of the display system will be described with reference to FIG. 14.

Figure 14:
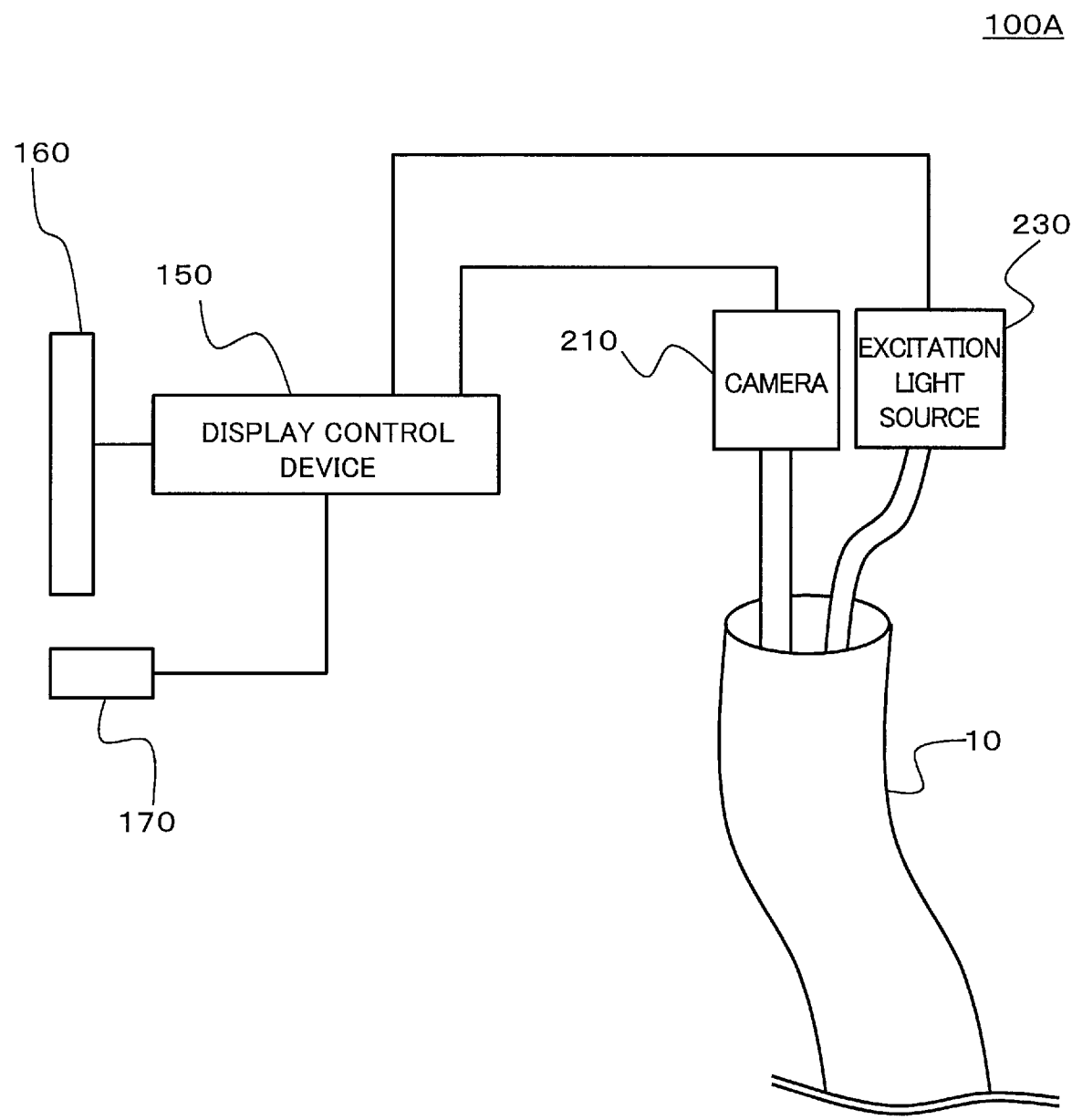
FIG. 14 is a diagram showing a configuration of a modified example of the display system.

FIG. 14 shows a configuration of an endoscope system 100A, which is a modified example of the display system. As shown in FIG. 14, the endoscope system 100A includes an endoscope 10, a camera 210, an excitation light source 230, a display control device 150, a monitor 160, and a mouse 170. Each device of the endoscope system 100A above other than the endoscope 10 is configured similarly to those in the surgery supporting system 100 in FIG. 1. The endoscope system 100A is a system that performs visual support related to fluorescence emission or the like in the body through display on the monitor 160, when the endoscope 10 is inserted into the body of a patient.

In the endoscope system 100A, for example, optical fibers constituting the endoscope 10 are individually connected to the camera 210 and the excitation light source 230. Similarly to the first embodiment, the camera 210 captures a fluorescence image and an object image. For example, each part in the body and an affected part that are inserted with the endoscope 10 are captured as an object in the object image.

In a normal mode of this system 100A, the display control device 150 performs processing similar to the image processing in the normal mode (S12 in FIG. 3) of the first embodiment on the basis of the fluorescence image from the camera 210, to generate a processed image. For example, the monitor 160 displays the processed image or displays an image in which the processed image is superimposed on the object image. Each of the above-described images is an example of a display image in this system 100A.

In an adjustment mode of this system, similarly to the first embodiment, the display control device 150 superimposes three images of the object image, the fluorescence image, and the processed image on each other to synthesize a superimposed image, and displays the superimposed image on the monitor 160 (see FIGS. 13A to 13D). Similarly to the adjustment mode of the first embodiment, the user can perform various kinds of adjustment on the superimposed image displayed on the monitor 160 by operating the mouse 170.

In each of the embodiments above, application examples of the display system in medical applications have been described, but the display system in the present disclosure is not limited to this. For example, the display system according to the present disclosure can be applied in a case where it is necessary to perform work on an object incapable of being visually checked for state change, such as in a construction site, a mining site, a building site, or a factory processing a material.

Specifically, a fluorescent material is applied, kneaded, or poured to an object incapable of being visually checked for state change, to provide a target of imaging by the camera 210, in a construction site, a mining site, a building site, a factory processing a material, and the like. Instead of light emission, a heat generating part may be detected with a thermal sensor, and that portion alone or a boundary alone may be scanned.

In each of the embodiments above, the example in which the camera 210 functions as both of the imager and the object imager has been described, but the present disclosure is not limited to this. The imager and the object imager may be constituted by separate cameras. In this case, it is possible to set, in each camera, a light reception characteristic for capturing the fluorescence image and a light reception characteristic for capturing the object image.

In each of the embodiments above, the superimposed image 7 obtained through image synthesis of the fluorescence image 5 and the projection image 6 is projected and displayed from one projector 220, but the present disclosure is not limited to this. For example, with use of a plurality of projectors constituting the display, the superimposed image may be displayed through individual projectors by coaxially superimposing and projecting the fluorescence image 5 and the projection image 6.

In each of the embodiments above, a description has been given with use of the optical unit 201 that transmits fluorescence generated from a photosensitive substance. However, the present disclosure is not limited to this, and a dichroic mirror or a prism that reflect or refract fluorescence may be used as an optical unit in the present disclosure. In this case, the arrangement of the camera 210 and the projector 220 may be changed as appropriate. Further, as the optical unit in the present disclosure, there may be used a polarizing plate or the like that changes a traveling direction of light of a predetermined polarization component. In this case, light can be selectively incident on the camera 210 or the projector 220 in accordance with the polarization component of the light.

As described above, the embodiments have been described as an example of the technique in the present disclosure. For this purpose, the accompanying drawings and detailed description have been provided.

Accordingly, some of the constituent elements described in the accompanying drawings and the detailed description may also include constituent elements that are not indispensable for solving the problem in order to exemplify the above technique, in addition to indispensable constituent elements for solving the problem. Therefore, these constituent elements that are not indispensable are not to be immediately recognized to be indispensable on the basis of the fact that these constituent elements that are not indispensable are described in the accompanying drawings or detailed description.

In addition, since the above-described embodiments are intended to exemplify the technique in the present disclosure, it is possible to make various changes, replacements, additions, omissions, and the like within the scope of claims or the equivalent thereof.

INDUSTRIAL APPLICABILITY

The display system according to the present disclosure can be applied in working on an object that is difficult to visually check for a state change, such as in a medical application, a construction site, a mining site, a building site, and a factory processing a material.

The invention claimed is:

1. A display system comprising:
an irradiator configured to irradiate an object with light having a wavelength in an invisible light region;
an imager configured to capture an invisible light image of the object and a visible light image of the object, the invisible light image being captured based on light excited by the light having the wavelength in the invisible light region, and the visible light image being captured based on light in a visible light region;
an image generator configured to generate a projection image based on the invisible light image;
a projector configured to project the projection image onto the object with visible light;
an optical system configured to align an optical axis of the imager and the projector;
a display configured to display a superimposed image in which the invisible light image and the projection image are displayed in a coaxially superimposed manner with each other without superimposing the visible light image; and
an adjuster configured to adjust the projection image included in the displayed superimposed image, based on a user operation, wherein
the adjuster adjusts the projection image by adjusting, based on a user operation, a threshold value for generating the projection image based on the invisible light image, and
the projector projects the adjusted projection image onto the object with visible light.

2. The display system according to claim 1, wherein the adjuster adjusts the projection image included in the displayed superimposed image by changing a transmittance of the projection image based on a user operation.

3. The display system according to claim 1, wherein the adjuster is further configured to adjust the invisible light image included in the displayed superimposed image by changing a transmittance of the invisible light image based on a user operation, and
the display displays the superimposed image using the adjusted invisible light image.

4. The display system according to claim 1, wherein the optical system transmitting a first light of a first wavelength band component and reflecting a second light of a second wavelength band component.

* * * * *